US012605420B2

(12) United States Patent
Su et al.

(10) Patent No.: US 12,605,420 B2
(45) Date of Patent: Apr. 21, 2026

(54) USE OF PLANT COMPOSITION, TRADITIONAL CHINESE MEDICINE COMPOSITION IN PREPARING MEDICINE FOR TREATING COVID-19

(71) Applicant: NATIONAL RESEARCH INSTITUTE OF CHINESE MEDICINE, MINISTRY OF HEALTH AND WELFARE, Taipei (TW)

(72) Inventors: Yi-Chang Su, Taipei City (TW); Wen-Hui Chiou, Taipei City (TW); Yuh-Chiang Shen, Taipei City (TW); Wen-Chi Wei, Taipei City (TW); Keng-Chang Tsai, Taipei City (TW); Chia-Ching Liao, Taipei City (TW); Yu-Hwei Tseng, Taipei City (TW); Chun-Tang Chiou, Taipei City (TW); Yu-Chi Lin, Taipei City (TW); Li-Hsiang Wang, New Taipei City (TW); Chien-Hsien Huang, Taipei City (TW); Chia-Mo Lin, New Taipei City (TW); Chi-Kuei Lin, New Taipei City (TW); Yi-Chia Huang, Taipei City (TW); Chien-Jung Lin, Taipei City (TW); Jui-Shan Lin, Taipei City (TW); Ya-Sung Yang, Taipei City (TW); Chun-Hsiang Chiu, Taipei City (TW); Shun-Ping Cheng, Taipei City (TW); Hsien-Hwa Kuo, Taoyuan City (TW); Wu-Pu Lin, Zhubei City (TW); Chen-Shien Lin, Taichung City (TW); Bo-Cheng Lai, Taipei City (TW); Yuan-Nian Hsu, Taoyuan City (TW); Tsung-Lung Tsai, Taoyuan City (TW); Wei-Chen Hsu, Taoyuan City (TW); Tieng-Siong Fong, Puxin Township, Changhua County (TW); Yi-Wen Huang, Puxin Township, Changhua County (TW); Chia-I Tsai, Taichung City (TW); Ya-Chen Yang, Taichung City (TW); Ming-Che Tsai, Taichung City (TW); Ming-Huei Cheng, Taichung City (TW); Shih-Wei Huang, Lukang Township, Changhua County (TW)

(73) Assignee: National Research Institute of Chinese Medicine, Ministry of Health and Welfare, Taipei City (TW)

( * ) Notice: Subject to any disclaimer, the term of this patent is extended or adjusted under 35 U.S.C. 154(b) by 690 days.

(21) Appl. No.: 18/047,712

(22) Filed: Oct. 19, 2022

(65) Prior Publication Data

US 2023/0122849 A1     Apr. 20, 2023

Related U.S. Application Data

(60) Provisional application No. 63/262,793, filed on Oct. 20, 2021.

(51) Int. Cl.
| | |
|---|---|
| A61K 36/00 | (2006.01) |
| A61K 36/076 | (2006.01) |
| A61K 36/282 | (2006.01) |
| A61K 36/428 | (2006.01) |
| A61K 36/539 | (2006.01) |
| A61K 36/575 | (2006.01) |
| A61K 36/704 | (2006.01) |
| A61K 36/714 | (2006.01) |
| A61K 36/78 | (2006.01) |
| A61K 36/8888 | (2006.01) |
| A61K 36/8969 | (2006.01) |
| A61P 11/00 | (2006.01) |
| A61P 31/14 | (2006.01) |
| A61K 36/484 | (2006.01) |

(52) U.S. Cl.
CPC .......... *A61K 36/714* (2013.01); *A61K 36/076* (2013.01); *A61K 36/282* (2013.01); *A61K 36/428* (2013.01); *A61K 36/539* (2013.01); *A61K 36/575* (2013.01); *A61K 36/704* (2013.01); *A61K 36/78* (2013.01); *A61K 36/8888* (2013.01); *A61K 36/8969* (2013.01); *A61P 11/00* (2018.01); *A61P 31/14* (2018.01); *A61K 36/484* (2013.01)

(58) Field of Classification Search
CPC .................................................... A61K 36/714
See application file for complete search history.

*Primary Examiner* — Qiuwen Mi
(74) *Attorney, Agent, or Firm* — SALIWANCHIK, LLOYD & EISENSCHENK

(57) ABSTRACT

The present invention relates to a method of treating moderate or severe symptoms of COVID-19 using a plant composition. The plant composition comprises Prepared Monkshood Daughter Root (*Aconitum carmichaelii*), Fragrant Solomonseal Rhizome (*Polygonatum odoratum*), Indian Bread (*Poria cocos*), Pinellia tuber (*Pinellia ternata*), Oriental Wormwood Herb (*Artemisia scoparia*), Scutellaria Root (*Scutellaria baicalensis*), Mongolian Snakegourd Fruit (*Trichosanthes kirilowii*), Magnolia Bark (*Magnolia officinalis*), Heartleaf Houttuynia Herb (*Houttuynia cordata*), and Baked Licorice Root and Rhizome (*Glycyrrhiza glabra*), which is used as a traditional Chinese medicine composition.

8 Claims, 24 Drawing Sheets
(13 of 24 Drawing Sheet(s) Filed in Color)

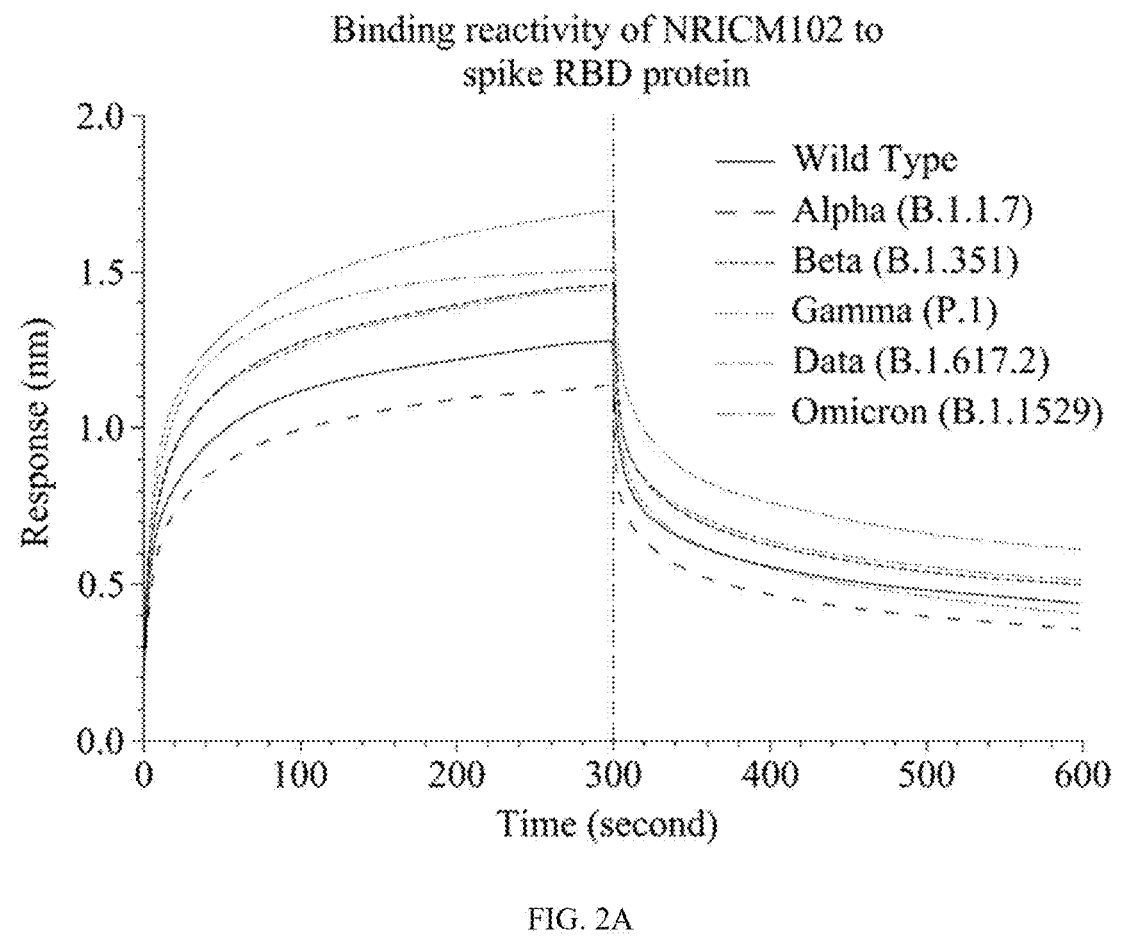

Binding reactivity of NRICM102 to
spike RBD protein

— Wild Type
– – Alpha (B.1.1.7)
—— Beta (B.1.351)
······ Gamma (P.1)
······· Data (B.1.617.2)
·-·-· Omicron (B.1.1529)

FIG. 2A

Saline

S1+NRICM102 (1.5 g)

S1+Saline

S1+NRICM102 (3.0 g)

Saline

Thrombin+Saline

Thrombin+NRICM102 (3.0 g)

| Treatment (3 days) | N | Survival (%) | OD (lung perfusion) | SO2% |
|---|---|---|---|---|
| Saline | 6 | 100 | 3.59 ± 0.13 | 96.5 ± 0.6 |
| S1 (400 µg/kg) | 6 | 100 | 1.72 ± 0.14 | 83.6 ± 3.7 |
| S1 + NRICM102 (1.5 g) | 6 | 100 | 2.50 ± 0.18* | 93.8 ± 2.4* |
| S1 + NRICM102 (3.0 g) | 6 | 100 | 2.78 ± 0.16* | 93.6 ± 1.0* |

FIG. 4D

| Treatment (5 days) | N | Survival (%) | OD (lung perfusion) | SO2% |
|---|---|---|---|---|
| Saline | 5 | 100 | 3.54 ± 0.04 | 98.0 ± 1.1 |
| Tb (50 U/kg) | 10 | 80 | 1.38 ± 0.18 | 95.7 ± 1.4 |
| Tb + NRICM102 (3.0 g) | 10 | 100* | 2.08 ± 0.17* | 94.6 ± 1.1 |

FIG. 4E

Ctrl

S1+Saline

S1+NRICM102

Ctrl

S1+Saline

S1+NRICM102

FN1

α-SMA

USE OF PLANT COMPOSITION, TRADITIONAL CHINESE MEDICINE COMPOSITION IN PREPARING MEDICINE FOR TREATING COVID-19

CROSS-REFERENCE TO RELATED APPLICATION

This application claims the benefit of prior-filed Provisional Application No. 63/262,793, filed on Oct. 20, 2021, in the United States Patent and Trademark Office, the disclosure of which is incorporated herein in its entirety by reference.

BACKGROUND OF THE INVENTION

1. Field of the Invention

The present invention relates to methods of treating COVID-19 using a plant composition and a traditional Chinese medicine composition, and particularly relates to a plant composition and a traditional Chinese medicine composition that can be used for treating coronavirus disease of 2019 (COVID-19).

2. Description of the Related Art

The infection of severe acute respiratory syndrome coronavirus 2 (SARS-COV-2)-induced novel coronavirus disease of 2019 (COVID-19) is first identified in Wuhan, China in December 2019, and the outbreak subsequently spread worldwide within a few months.

COVID-19 is a global pandemic. As of November 2020, there have been more than 50 million confirmed cases and more than 1.2 million deaths. Scientists around the world are accelerating the development of effective treatments which is mainly symptomatic treatment, such as antiviral agents that target spike protein (Dalbavancin and Ceftazidime), the 3CL protease (Paxlovid) and RNA-dependent RNA polymerase inhibitors (Remdesivir and Molnupiravir). However, its therapeutic effect is not significant. Therefore, the therapeutic effects of various existing drugs in treating COVID-19 are still inconclusive.

In addition, countries are currently using vaccines against COVID-19 to prevent patients from becoming infected. The current internationally certified vaccines include BNT, Moderna, AZ, and Johnson & Johnson. Although some of the vaccines have higher protection rates, at this stage, new variants of the coronavirus are also discovered. Vaccination can greatly improve resistance, but it is still difficult to prevent the mutated variants. Many people who have received two doses of vaccine or a third dose of supplementary vaccine are still unfortunately infected, and there are still cases with moderate or severe symptoms.

Furthermore, even after the infected patients recover, there are still many sequelae, such as heart palpitations, hair loss, dyspnea, impaired lung function, intelligence decline, etc. In particular, the effect of impaired lung function is large and is likely to permanently affect oxygen exchange function.

There has been a traditional Chinese medicine composition developed by the inventors of the present invention, that is, a traditional Chinese medicine composition for relieving mild symptoms of COVID-19 developed by National Research Institute of Chinese Medicine of Taiwan. Taiwan Chingguan Yihau is composed of *Scutellaria* Root, Heartleaf *Houttuynia*, Indigowoad root, *Trichosanthes* Fruit, Fineleaf

*Nepeta*, Peppermint herb, Mulberry leaf, *Magnolia* Bark, Baked Liquorice root, and *Sposhnikovia* root and Rhizome.

At present, Taiwan Chingguan Yihau has only improved the mild symptoms of COVID-19, but still has no obvious therapeutic effect on moderate or severe symptoms of COVID-19. Therefore, on the basis of Taiwan Chingguan Yihau, the inventors of the present invention further modified some of the plant components to obtain a novel plant composition, which can be used as a traditional Chinese medicine composition for treating moderate or severe symptoms of COVID-19.

SUMMARY OF THE INVENTION

In view of the above-mentioned problems in the prior art, an objective of the present invention is to provide a novel plant composition, which can be used as a traditional Chinese medicine composition to treat patients with moderate or severe symptoms of COVID-19 infection.

The plant composition of the present invention is composed of Prepared Monkshood Daughter Root (*Aconitum carmichaelii*), Fragrant Solomonseal Rhizome (*Polygonatum odoratum*), Indian Bread (*Poria cocos*), Pinellia tuber (*Pinellia ternata*), Oriental Wormwood Herb (*Artemisia scoparia*), Scutellaria Root (*Scutellaria baicalensis*), Mongolian Snakegourd Fruit (*Trichosanthes kirilowii*), Magnolia Bark (*Magnolia officinalis*), Heartleaf *Houttuynia* Herb (*Houttuynia cordata*), and Baked Licorice Root and Rhizome (*Glycyrrhiza glabra*), and is served as a traditional Chinese medicine composition, named Taiwan Chingguan Erhau or NRICM102. In the plant composition, the amount of each botanical component in parts by weight of an aqueous extract is as follows: 1 part by weight of an aqueous extract of Prepared Monkshood Daughter Root (*Aconitum carmichaelii*), 1.5 parts by weight of an aqueous extract of Fragrant Solomonseal Rhizome (*Polygonatum odoratum*), 2.5 parts by weight of an aqueous extract of Indian Bread (*Poria cocos*), 1.5 part by weight of an aqueous extract of Pinellia tuber (*Pinellia ternata*), 2.5 parts by weight of an aqueous extract of Oriental Wormwood Herb (*Artemisia scoparia*), 1.5 parts by weight of an aqueous extract of Scutellaria Root (*Scutellaria baicalensis*), 2.5 parts by weight of an aqueous extract of Mongolian Snakegourd Fruit (*Trichosanthes kirilowii*), 1.5 parts by weight of an aqueous extract of Magnolia Bark (*Magnolia officinalis*), 5 parts by weight of an aqueous extract of Heartleaf *Houttuynia* Herb (*Houttuynia cordata*), and 1 part by weight of an aqueous extract of Baked Licorice Root and Rhizome (*Glycyrrhiza glabra*).

When the plant composition is used as a traditional Chinese medicine composition, a method of preparation of the traditional Chinese medicine composition includes mixing Prepared Monkshood Daughter Root (*Aconitum carmichaelii*), Fragrant Solomonseal Rhizome (*Polygonatum odoratum*), Indian Bread (*Poria cocos*), Pinellia tuber (*Pinellia ternata*), Oriental Wormwood Herb (*Artemisia scoparia*), Scutellaria Root (*Scutellaria baicalensis*), Mongolian Snakegourd Fruit (*Trichosanthes kirilowii*), Magnolia Bark (*Magnolia officinalis*), Heartleaf *Houttuynia* Herb (*Houttuynia cordata*), and Baked Licorice Root and Rhizome (*Glycyrrhiza glabra*), adding water therein, boiling and condensing the water to approximately ¼ volume to obtain a decoction which is the traditional Chinese medicine composition.

The traditional Chinese medicine composition has been studied and found to have a positive effect on the treatment of lung injury, and can improve the lung function and mortality of patients with moderate or severe symptoms of COVID-19. The traditional Chinese medicine composition can inhibit the binding of the spike protein of coronavirus to type II angiotensin-converting enzyme 2 (ACE2), inhibit the activity of viral 3CL protease, reduce the activation of monocytes and neutrophils, and reduces various cytokines expression, thereby blocking viral infection and progression to lung damage caused by pulmonary embolism and pulmonary fibrosis.

Please refer to FIG. 1, which is a schematic diagram of the potential pathway of severe acute respiratory syndrome coronavirus 2 (SARS-COV-2) infection and the method of the traditional Chinese medicine composition of the present invention to block viral infection. As shown in the figure, the infection mechanism of coronavirus is that the spike protein binds to type II angiotensin-converting enzyme 2 (ACE2), which reduces type II alveolar cells and impairs the replacement of type I alveolar cells. The affected alveolar repairment induces epithelial mesenchymal transition (EMT), i.e., fibrosis. In addition, because the ACE2 is reduced by binding with the spike protein of coronavirus, the overactivation of type II angiotensin (angiotensin II) and type I alveolar cell receptor axis (receptor axis) exacerbates the tissue-destroying effects of inflammatory response, increases production of plasminogen activator inhibitor-1 (PAI-1), reduces plasmin activation and fibrinolysis, and leads to fibrosis.

Coronavirus infection triggers type I alveolar cells, type II alveolar cells, and endothelial cells to release cytokines, which cause increased capillary permeability, enabling adhesion and extravasation of neutrophils and monocytes into alveolar interstitial space. When stimulated by pathogen-related and damage-related molecular patterns (PAMPs and DAMPs), neutrophils and macrophages secrete massive amounts of cytokines, procoagulants, and complements, which further induces vascular injury, enhancing the risk for thrombosis.

The key factors of thrombosis formation are as follows:
1. Neutrophil-mediated secretion of neutrophil extracellular traps (NETs) and von Willebrand factor (vWF) upregulation on cytokine-/virus-activated endothelial, cells or macrophages occur, and lung residential megakaryocytes produce locally available platelets, which enhances platelet aggregation.
2. Cytokine-triggered secretion of tissue factor (TF) by endothelial cells and macrophages stimulates the coagulation cascade and increases fibrin clot formation.
3. Overactivation of the angiotensin-converting enzyme, angiotensin II, AT1 receptor axis increases production of plasminogen activator inhibitor 1 (PAI1), reducing plasmin activation and fibrinolysis.

Using the traditional Chinese medicine composition of the present invention, the chain effect caused by the binding of type II angiotensin converting enzyme and the spike protein of coronavirus is blocked, the apoptosis of type I and/or type II alveolar cells is reduced, and the inflammatory response is down-regulated, including activation of neutrophils and monocytes, release of cytokines (TNF-α, IL-6, MCP-1, etc.) and expression of inflammatory receptors (TLR4). Pro-thrombotic factor (vWF and PAI-1) and fibrosis factors (c-Kit, FN1, and SCF, etc.) are reduced, thereby reducing pulmonary embolism and pulmonary fibrosis in patients with moderate or severe symptoms of COVID-19.

Hereinafter, the actual efficacy of the traditional Chinese medicine composition of the present invention will be proved by the specific examples and the obtained experimental data.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The detailed technical features, content and advantages of the present invention will now be described in more details hereinafter with reference to the accompanying drawings that show various embodiments of the invention as follows

FIGS. 2A and 2B are schematic diagrams of the inhibitory effect of NRICM102 on the binding of the spike protein of SARS-COV-2 to ACE2. FIG. 2A is analyzed by BioLayer Interferometry (BLI), and FIG. 2B is analyzed by enzyme linked immunosorbent assay (ELISA);

FIGS. 4A-4E are schematic diagrams of the therapeutic effect of NRICM102 on pulmonary embolism induced by SARS-COV-2 spike protein and thrombin, and test simplified flow diagram thereof.

DETAILED DESCRIPTION OF THE PREFERRED EMBODIMENTS

Figure 1:
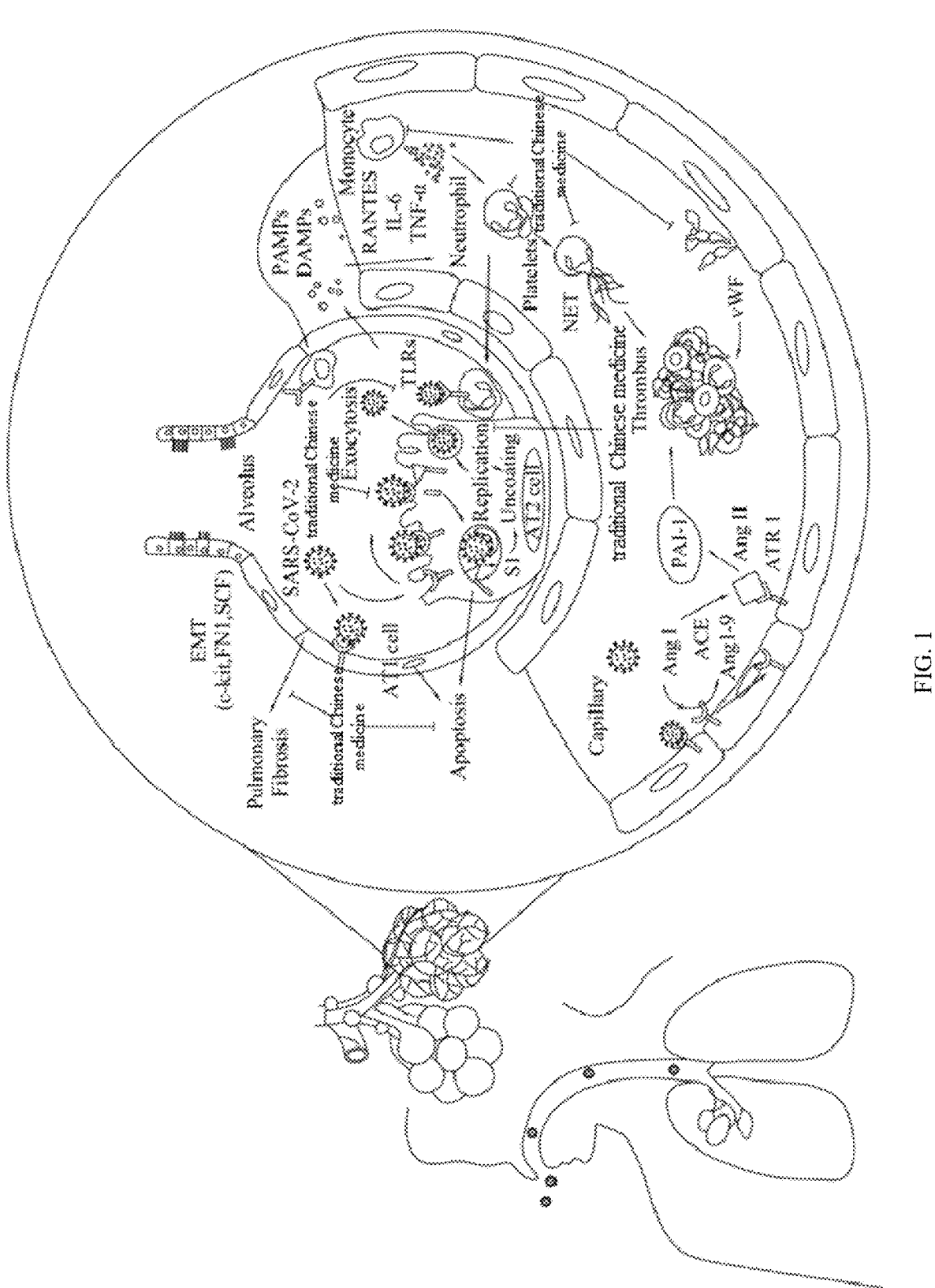
FIG. 1 is a schematic diagram of the potential pathway against SARS-COV-2 infection and the method of the traditional Chinese medicine composition of the present invention to block viral infection.

The technical content of the present invention will become apparent by the detailed description of the following embodiments and the illustration of related drawings as follows. The main purpose of the drawings used herein is only for illustration and auxiliary description, and may not be of real scale and precise configuration in actual implementation of the present invention Therefore, the scope of the present invention should not be interpreted or limited based on the ratio and configuration relationship of the attached drawings.

Unless otherwise defined, all the terms (including technical and scientific terms) used herein have the same meaning as commonly understood by one of ordinary skill in the art to which the present invention belongs. It will be further understood that terms such as those defined in commonly used dictionaries should be construed as having meanings consistent with the meanings in the context of the related art and the present invention, and are not to be construed as idealized or excessive formal meaning unless clearly defined herein.

All numerical values herein are understood to be modified by "about." The term "about" as used herein means to encompass a variation of +10%.

Materials and Methods

Human bronchial epithelial cells (BEAS-2B) were purchased from Bioresource Collection and Research Center (BCRC, Taiwan); recombinant SARS-COV-2 spike protein subunit 1 (S1) was purchased from GeneTex International Corporation (UK, product number GTX135817-pro); lipopolysaccharide (*Escherichia coli*, 055: B5) and bleomycin were purchased from Sigma (USA); the traditional Chinese medicine composition (NRICM102) was prepared by the Chinese Herbal Medicine Pharmacy in Taichung Veterans General Hospital.

Experimental animals were 6-8-week-old male C57BL/6 and ICR mice, purchased from the National Laboratory Animal Breeding and Research Center (Taipei, Taiwan); 14-16-week-old male K18-hACE2 transgenic mice were purchased from Jackson Laboratory and inbred at the Laboratory Animal Center of National Taiwan University College of Medicine. All experimental animals were treated with standard environmental and food conditions, namely 22±1° C., 55±5% humidity, and 12-hour light/dark cycle, with free access to food and water; all experimental animals were randomized into double-blind manner to reduce experimental bias.

Preparation Example 1

Traditional Chinese Medicine Composition and Method for Preparing the Same

The traditional Chinese medicine composition of the present invention comprises Prepared Monkshood Daughter Root (*Aconitum carmichaelii*), Fragrant Solomonseal Rhizome (*Polygonatum odoratum*), Indian Bread (*Poria cocos*), Pinellia tuber (*Pinellia ternata*), Oriental Wormwood Herb (*Artemisia scoparia*), Scutellaria Root (*Scutellaria baicalensis*), Mongolian Snakegourd Fruit (*Trichosanthes kirilowii*), Magnolia Bark (*Magnolia officinalis*), Heartleaf Houttuynia Herb (*Houttuynia cordata*), and Baked Licorice Root and Rhizome (*Glycyrrhiza glabra*), which is the formula of Taiwan Chingguan Erhau (NRICM102). The dosages of the ten kinds of Chinese medicine are shown in Table 1 below (the grams (g) of each ingredient herein are exemplary, and the corresponding grams and the corresponding amount of decoction water can be adjusted according to the weight portion ratio).

TABLE 1

| Ingredient of the traditional Chinese medicine composition | content(g) | content (parts by weight of an aqueous extract) |
|---|---|---|
| Prepared Monkshood Daughter Root (*Aconitum carmichaelii*) | 7.50 | 1 |
| Fragrant Solomonseal Rhizome (*Polygonatum odoratum*) | 11.25 | 1.5 |
| Indian Bread (*Poria cocos*) | 18.75 | 2.5 |
| Pinellia tuber (*Pinellia ternata*) | 11.25 | 1.5 |
| Oriental Wormwood Herb (*Artemisia scoparia*) | 18.75 | 2.5 |
| Scutellaria Root (*Scutellaria baicalensis*) | 11.25 | 1.5 |

TABLE 1-continued

| Ingredient of the traditional Chinese medicine composition | content(g) | content (parts by weight of an aqueous extract) |
|---|---|---|
| Mongolian Snakegourd Fruit (*Trichosanthes kirilowii*) | 18.75 | 2.5 |
| Magnolia Bark (*Magnolia officinalis*) | 11.25 | 1.5 |
| Heartleaf Houttuynia Herb (*Houttuynia cordata*) | 37.50 | 5 |
| Baked Licorice Root and Rhizome (*Glycyrrhiza glabra*) | 7.50 | 1 |

The ten kinds of Chinese medicine described in Table 1 are mixed and put into a boiler, add 1.2 L of water for decoction, decocting to boiling point, and boil until the water is concentrated to 300 mL (that is, concentrated to about ¼ volume of water, and the concentrated water is about 40 parts by weight) to obtain a decoction, which is the traditional Chinese medicine composition (NRICM102, which will be used hereinafter).

Embodiment 1

ACE2-Spike Protein Binding and NRICM102 Binding Test:

Biolayer interferometric binding events were detected and monitored in real time using a FortéBio Octet Red 96e Biolayer Interferometer (Molecular Device). First, different variants of recombinant SARS-COV-2 variant RBD proteins (purchased from Sino Biological) were immobilized on the HISIK sensor tip at a concentration of 100 µg/mL in phosphate buffered saline (PBS) for 600 seconds, followed by blocking the sensor tip with 1% bovine serum albumin (BSA) for 5 minutes; NRICM102 was resuspended in kinetic buffer (PBST, NaCl adjusted to a concentration of 350 mM), and MRICM102 was 5-fold diluted. After that, each sample (recombinant SARS-COV-2 variant RBD protein of different variants) was added, and the steps of baseline, association and dissociation were used to perform binding tests for 60 seconds, 300 seconds, and 600 seconds is performed in sequence respectively, the sensor tip generates atypical binding events to immobilized protein through non-specific binding effect; then, the correlation signals and curves were aligned to the test data with a 1:1 best fit model using FortéBio data analysis software. In addition, reference sensor subtraction was used to reduce the signal associated with atypical binding events, i.e., a set of blank sensors that were individually unloaded with protein were exposed to predetermined conditions.

Results

Please refer to FIG. 2A, FIG. 2A is analyzed by BioLayer Interferometry (BLI). In the case of administering 5-fold dilution of NRICM102, NRICM102 can bind to the spike proteins of various SARS-COV-2-related variants, among which NRICM102 has the highest binding activity for the Delta variant, followed by the Omicron variant, the Beta variant, the Gamma variant, Wild Type, and the Alpha variant.

Embodiment 2

ACE2-Spike Protein Inhibition Enzyme-Linked Immunosorbent Assay (ELISA)

Microplates were coated with recombinant SARS-COV-2 variant RBD protein (0.1~2 µg/well), and after blocking with 1% bovine serum albumin (BSA) for 1 hour at 37° C., NRICM102 was serially diluted (⅒×, 1/50×, 1/100×, 1/150×, $\frac{1}{300}\times$, $\frac{1}{600}\times$, $\frac{1}{900}\times$, $\frac{1}{1200}\times$, $\frac{1}{1500}\times$, $\frac{1}{2000}\times$, $\frac{1}{3000}\times$, and $\frac{1}{6000}\times$) and added to the wells, reacted with recombinant SARS-COV-2 variant RBD protein at 37° C. After the reaction was completed, hACE2 recombinant protein (0.2 µg/mL.) was added to each well and incubated at 37° C. for 40 minutes, and then rabbit anti-human IgG-HRP (purchased from Immunology consultants laboratories, Inc.) was added to each well and incubated for 40 minutes. Then the HRP matrix 3,3',5,5'-tetramethylbenzidine was added to each well for color development, and 1N HCl was used to terminate the reaction after color development was completed, and the signal intensity was quantified at OD 450 nm using a spectrometer. The recombinant SARS-COV-2 variant RBD spike proteins used include Alpha (B.1.1.7), Beta (B.1.351), Gamma (P.1), Delta (B.1.617.2), Omicron (B.1.1529) and the original wild-type coronavirus.

Results

Figure 2B:
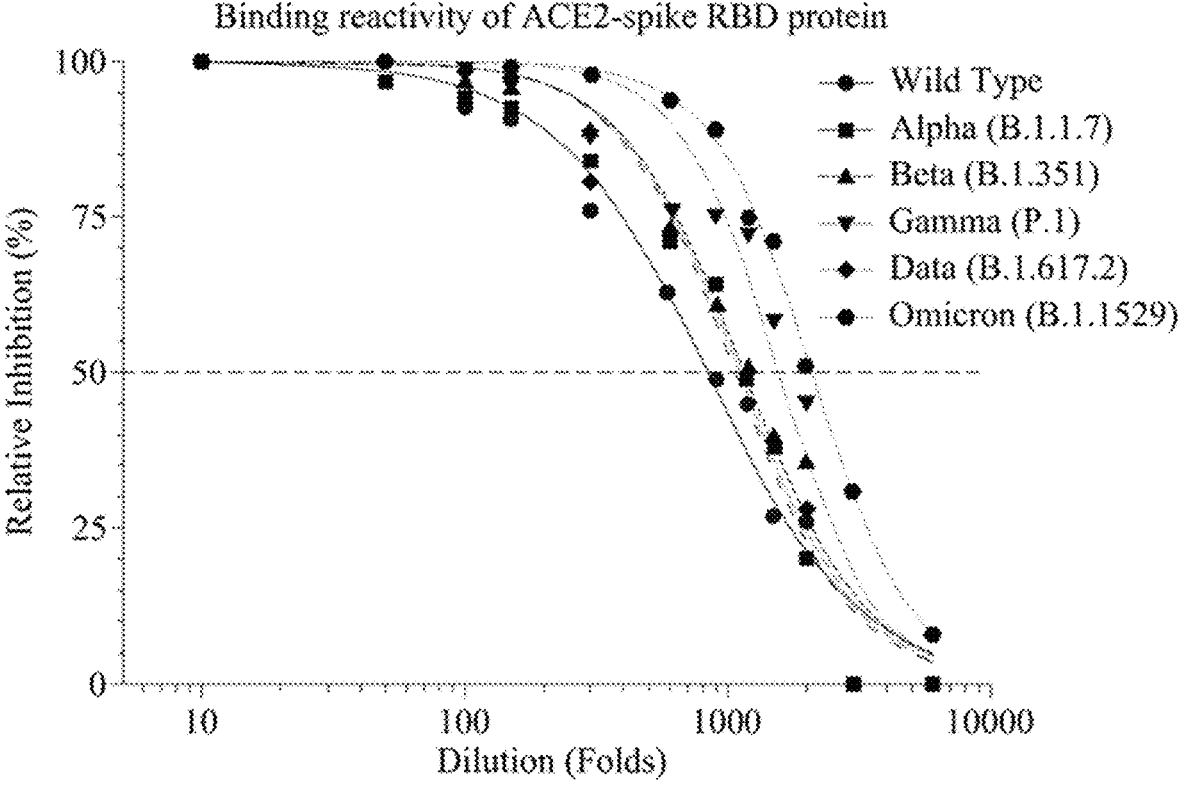

Please refer to FIG. 2B, FIG. 2B shows the effect of the administration of different dilution concentrations of NRICM102 on inhibiting the binding activity of SARS-COV-2 spike protein and ACE2. As shown in the figure, the $EC_{50}$ of NRICM102 for various SARS-COV-2 related variants is as follows: 2090-fold dilution for Omicron variant, 1571-fold dilution for Gamma variant, 1151-fold dilution for Beta variant, 1117-fold dilution for Delta variant, 1068-fold dilution for Alpha variant, and 833.9-fold dilution for the wild type. From the results above, it can be seen that the antiviral properties of NRICM102 still have significant effects on different SARS-COV-2 variants.

Embodiment 3

Figure 3:
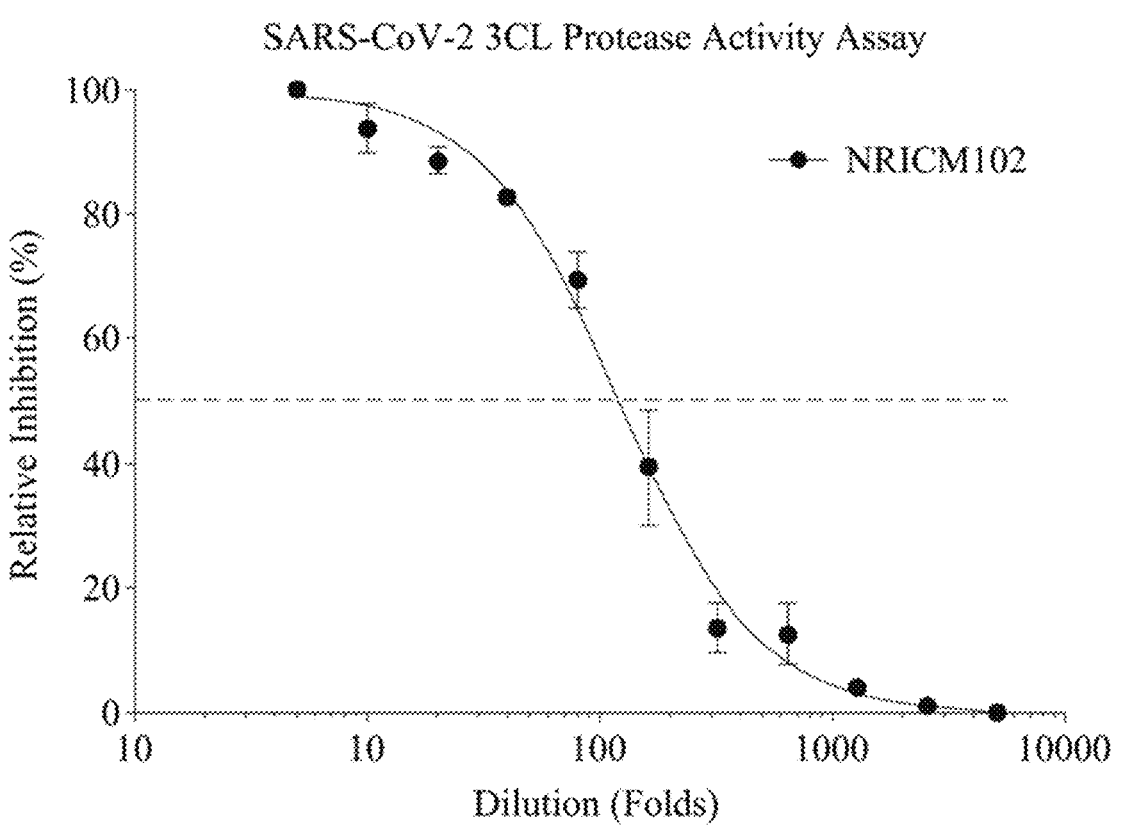
FIG. 3 is a schematic diagram of the inhibitory effect of NRICM102 on 3CL protease of SARS-COV-2.

3CL Protease Inhibition Assay:

Recombinant SARS-COV-2 3CL protease (purchased from Pharmtekx, Taipei, Taiwan) was incubated with NRICM102 in reaction buffer (25 mM Tris, 100 mM NaCl, 1 mM EDTA, 1 mM DTT, pH 7.3) on ice for 30 min. A luciferase matrix peptide (Dabcyl-KTSAVLQSGFRKME (Edans)-OH, purchased from Kelowna International Scientific Inc., New Taipei City, Taiwan) was then added to induce a proteolytic reaction; Cytation 5 cell imaging multifunctional optical detector (BioTek, Vermont, USA) was used to excite the sample at 355 nm for 1 hour at 37° C., and the reaction was monitored at 538 nm, inhibition was calculated and graphed with GraphPad Prism graphing software. Results:

Please refer to FIG. 3, FIG. 3 is a schematic diagram of the inhibitory effect of NRICM102 on the 3CL protease of SARS-COV-2. As shown in the figure, NRICM102 has a significant inhibitory effect on 3CL protease, and its IC 50 is 119-fold dilution; therefore, the results prove that NRICM102 has a significant inhibitory effect on 3CL protease activity

Embodiment 4

Therapeutic test of recombinant SARS-COV-2 spike protein subunit 1 (spike protein subunit 1, S1)-induced pulmonary embolism in K18-hACE2 mice and thrombin (Thrombin)-induced pulmonary embolism in ICR mice Mice were anesthetized with intraperitoneal injection of xylazine (6 mg/kg) and ketamine (60 mg/kg). A small skin incision was created on the neck of each mouse. S1 (400 µg/kg in 2 mL/kg) was dissolved in sterile normal saline and instilled into the tracheal lumen. The incision was closed after instillation to allow the mice to recover. Mice treated as above were orally administered NRICM102 (1.5 g/kg or 3.0 g/kg) or vehicle (saline, as control group) daily for 3 consecutive days, then sacrificed the mice to collect lungs; the groups were as follows: Saline control group (Ctrl), S1+saline, S1+NRICM102 (1.5 g), and S1+NRICM102 (3.0 g).

Using lung perfusion detection, mice were perfused with 0.5 mL of 1% Evans blue through the right ventricle. The mouse lungs were then excised and photographed, and the degree of vascular occlusion was evaluated independently by detecting the optical density (OD, absorbance at 620 nm) of Evans blue, the percentage of hemoglobin bound with oxygen, was measured using an iSTAT G3+ detection kit (Abbott Point of Care Canada Limited, Canada).

Before sacrificing the mice, the distance traveled in a behavioral observation box ($60\times40\times60$ cm$^3$) was tracked for 3 minutes to assess the movement activity of the mice, and thereafter an image tracking system (SMART v2.5.21, Pan-lab, Spain) was used to analyze the results; survival rate was calculated immediately (day 0) and 72 hours (day 3) after administration of S1.

The method for thrombin induced pulmonary embolism in ICR mice was by injection of α-thrombin (50 U/kg, bovine, Sigma-Aldrich, St. Louis, USA) through the inferior vena cava in 100 µL of sterile saline to induce acute pulmonary embolism in mice. The groups were as follows: saline control group (Ctrl), thrombin, and thrombin+NRICM102 group (3.0 g/kg/day, oral administration for 5 days). The analysis method is the same as the above-mentioned lung perfusion test, pulmonary blood oxygen saturation test and exercise observation; the survival rate is also calculated in the same manner as mentioned above.

Results

Please refer to FIGS. 4A-4E, FIGS. 4A-4E are schematic diagrams of the therapeutic effect of NRICM102 on pulmonary embolism induced by SARS-COV-2 spike protein, and thrombin, and test simplified flow diagram thereof. From FIGS. 4B and 4D, it can be seen that the spike protein subunit 1 (S1) caused the lung perfusion to decrease by about 52%, from 3.59+0.13 (control group) to 1.72+0.14, and the pulmonary oxygen saturation decreased significantly from 96.5+0.6 to 83.6+3.7%; after 3 consecutive days of treatment with different doses of NRICM102, lung perfusion returned to 2.50+0.18 (1.5 g/kg of NRICM102) and 2.78+0.16 (3.0 g/kg of NRICM102), and the pulmonary oxygen saturation of both also recovered to greater than about 93%. Therefore, NRICM102 indeed significantly improve the pulmonary embolism induced by S1.

Figure 4A:
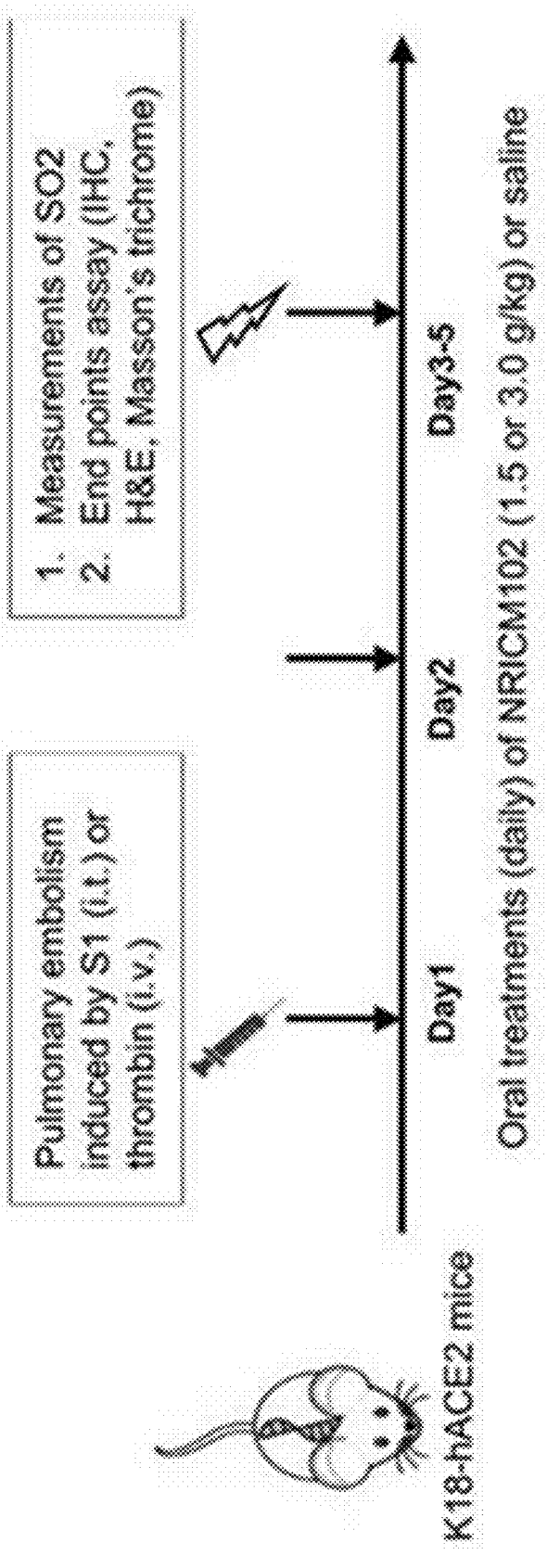
Figures 4B, 4C:
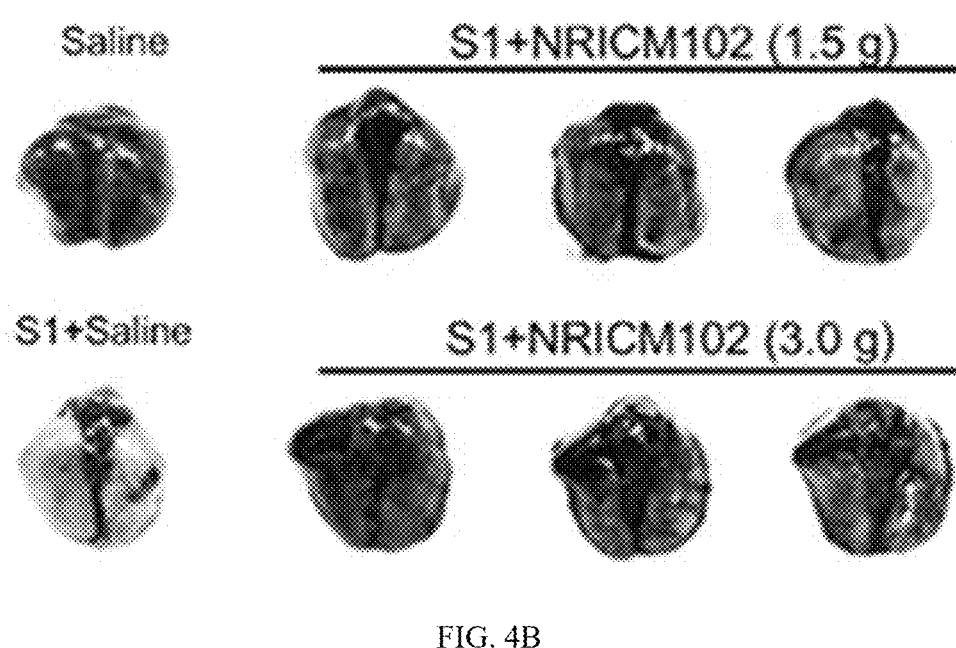

As shown in FIGS. 4C and 4E, thrombin also induced significant pulmonary embolism, killing 40% of the mice within 5 days and causing a decrease in lung perfusion by about 60% (from 3.54+0.04 to 1.38+0.18). After administration of 3.0 g/kg of NRICM102 for 5 consecutive days, the survival rate of mice was significantly improved to 100%, and the pulmonary perfusion recovered to 2.08+0.17 (p<0.05, with statistical significance). However, there were no significant differences in pulmonary oxygen saturation and animal mobility among the groups on day 5.

Therefore, the results prove that NRICM102 has significant therapeutic effect on pulmonary embolism caused by SARS-COV-2 and thrombin.

Embodiment 5

Therapeutic Test of Bleomycin (BLM)-Induced Lung Injury in C57BL/6 Mice

Mice were anesthetized with intraperitoneal injection of xylazine (6 mg/kg) and ketamine (60 mg/kg). A small skin incision was made on the neck of each mouse. BLM (2 U/kg, purchased from Sigma) was dissolved in 40 μL of phosphate-buffered saline (PBS) and instilled into the tracheal lumen. After inoculation, the incision was closed, and the animal was allowed to recover. Mice treated as above were orally administered NRICM102 (1.5 g/kg or 3.0 g/kg) or vehicle (saline, as control group) daily for 20 consecutive days before sacrifice. During day 0 to day 21 after bleomycin administration, the mouse body weight and its survival rate were calculated (20% reduction of mouse body weight was selected as the end point of humane sacrifice), and the mouse lung function was measured by conventional plethysmography.

Results

Figure 5A:
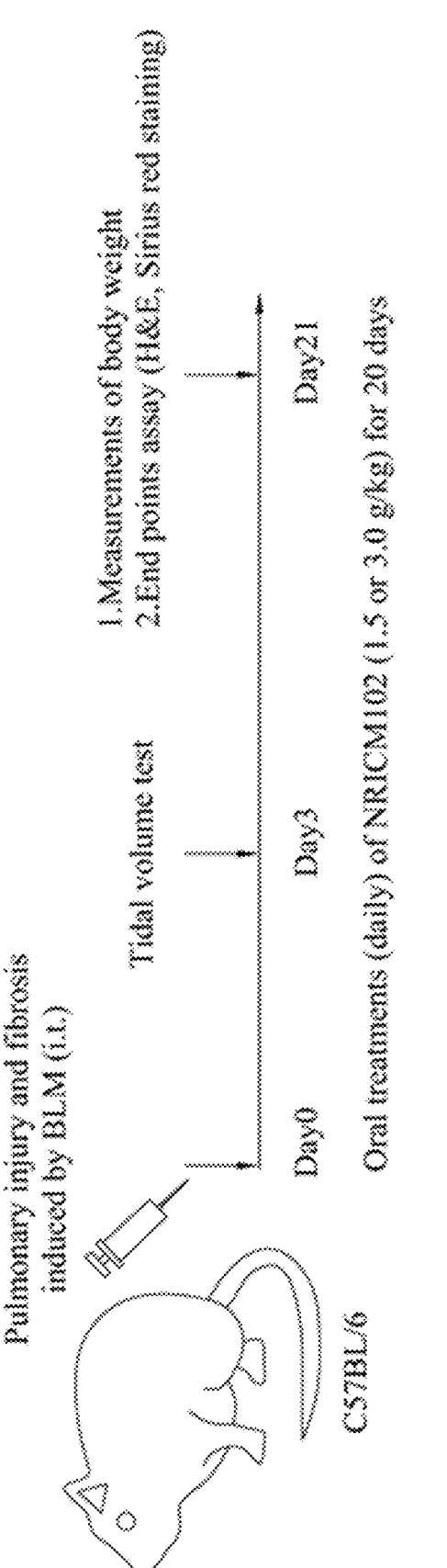
FIGS. 5A-5E are schematic diagrams of the therapeutic effect of NRICM102 on bleomycin-induced lung injury, and test simplified flow diagram thereof.
Figure 5B:
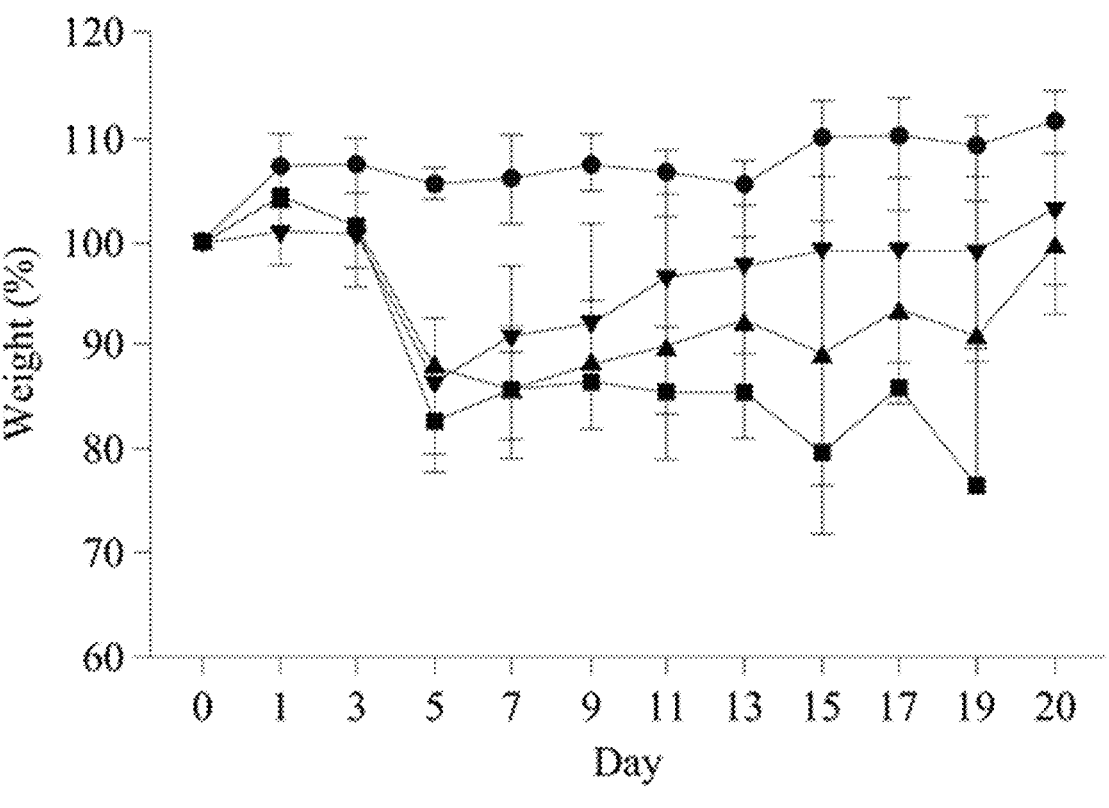
Figure 5C:
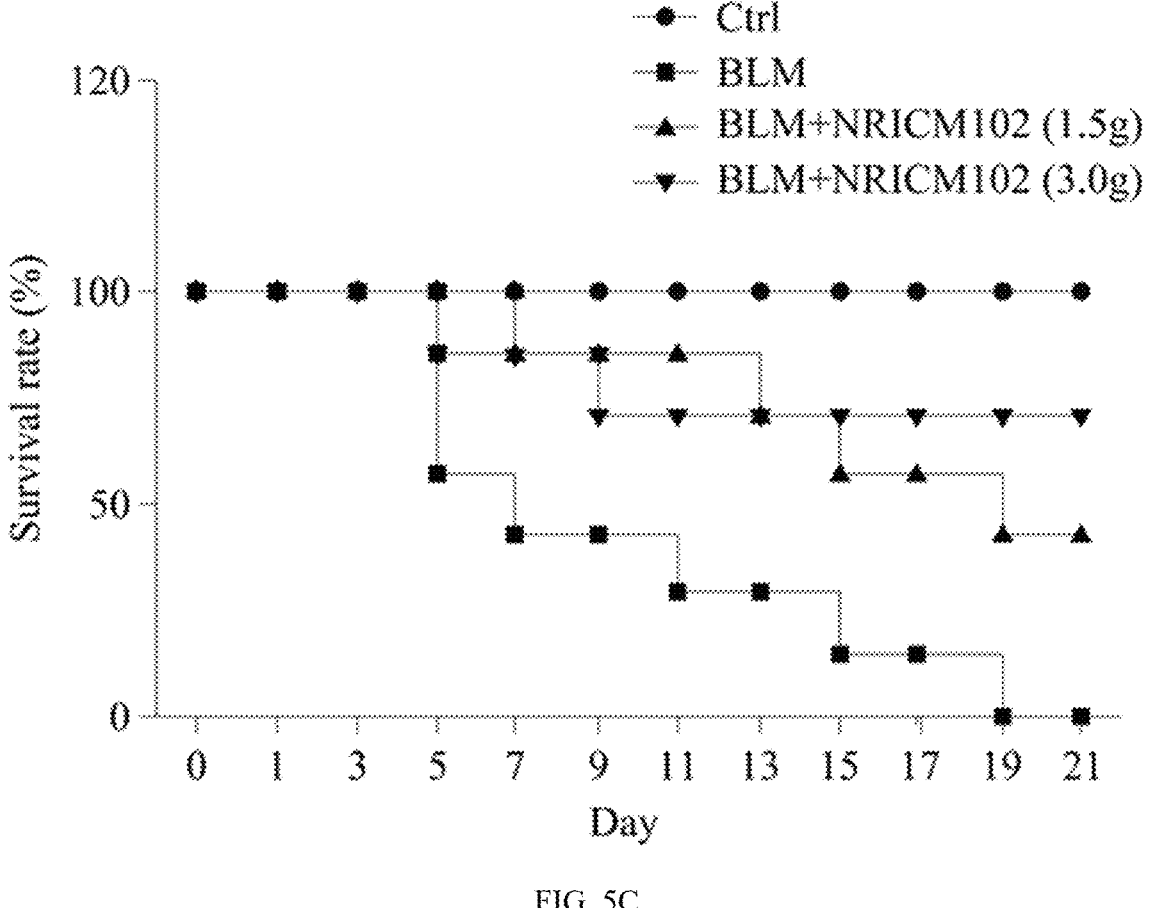

Please refer to FIGS. 5A-5E, FIGS. 5A-5E are schematic diagrams of the therapeutic effect of NRICM102 on bleomycin-induced lung injury, and test simplified flow diagram thereof. As shown in FIG. 5B and FIG. 5C, compared with the control group, the mice administered bleomycin (BLM) showed significant weight loss on the 5th day, and the survival rate of the mice decreased significantly from the 7th day. The survival rate dropped to 0% on the $21^{st}$ day. On the other hand, administration of NRICM102 significantly improved the phenomenon of BLM-induced weight loss, the survival rate of NRICM102 administration of 1.5 g/kg and 3.0 g/kg increased to 42.8% and 71.4%, respectively.

Figure 5D:
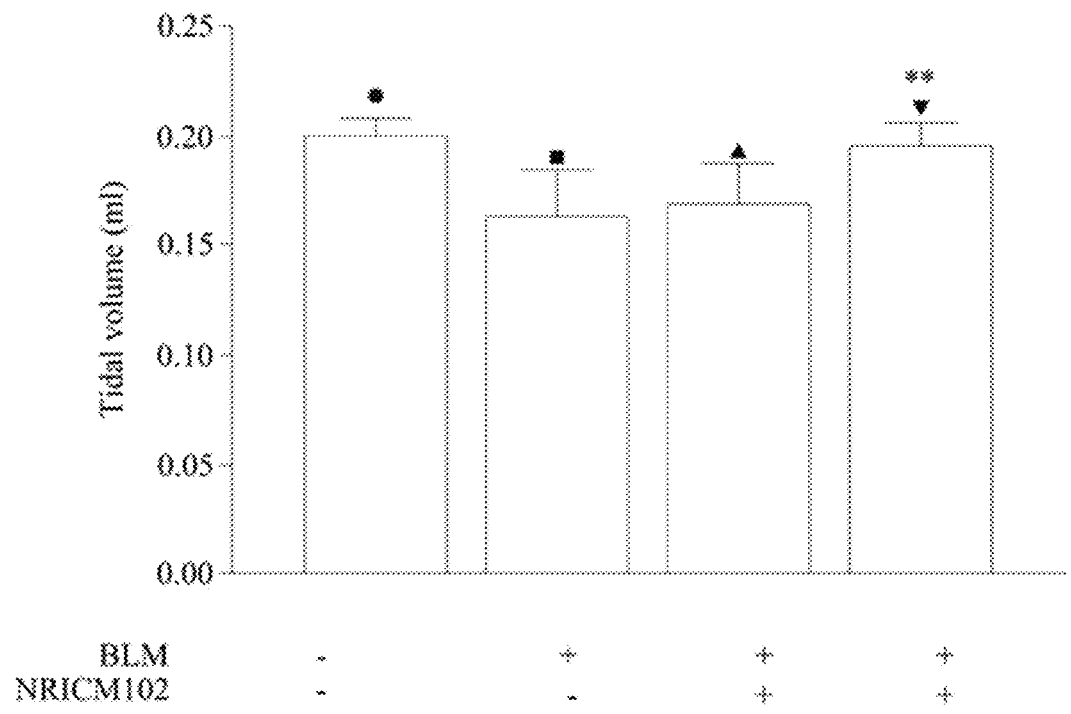
Figure 5E:
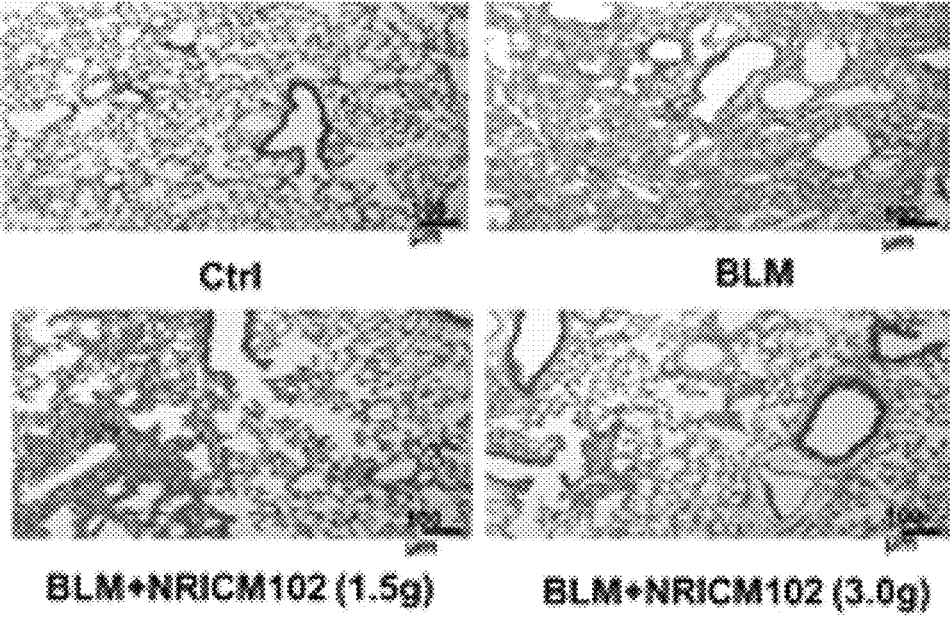

Lung tidal volume of mice was measured 3 days after bleomycin-induced lung injury. As shown in FIG. 5D, administration of NRICM102 (3.0 g) significantly reduced bleomycin-induced tidal volume. In addition, by staining with hematoxylin and eosin stain (H&E stain), FIG. 5E shows that the groups administered with NRICM102 have significantly improved the bleomycin-induced lung injury.

Therefore, the results prove that NRICM102 has significant therapeutic effect on pulmonary embolism caused by bleomycin.

Embodiment 6

Histopathological and Immunohistochemical Tests:

For immunohistochemical (IHC) staining, 15-20 consecutive sections (about 20-30 μm in thickness) of the same level of lung tissue were collected from different experimental groups for staining. All tissue sections were fixed, permeabilized and blocked and were randomly selected for specific marker staining with primary antibodies (diluted in PBS containing 3% albumin at 4° C. overnight).

Antibodies against S1 RBD (1:100) and citrulline histone H3 (CitH3, NET, 1:50), Ly6G (1:100), MPO (1:100), vWF (1:100), PAI-1 (1:100), PDPN (AT1, 1:100), SFTPC (AT2, 1:100), MIF (1:100) and TLR4 (1:100) were purchased from GeneTex (Irvine, CA, USA); Antibodies against CD11b (1:50) and CD31 (also known as platelet endothelial cell adhesion molecule 1, PECAM-1) were purchased from Abcam (Cambridge, UK). SCF (1:50) and cCasp3 (1:50) antibodies were purchased from Santa Cruz (Santa Cruz Biotechnology, Inc., CA, USA); p-NFκB P65 antibody was purchased from BD Pharmingen (1:50, BD Pharmingen, San Diego, CA, USA), and c-Kit antibody was purchased from Invitrogen (1:200, Invitrogen, Frederick, MD, USA).

After washing, all the sections were stained with secondary antibodies conjugated with Alexa Fluor® 488, Alexa Fluor® 555, or Alexa Fluor® 647 (all purchased from Cell Signaling Technology Inc., MA, USA). In order to counterstain the DNA in the nuclei, all sections on coverslips were mounted with medium containing 4',6-diamidino-2-phenylindole (DAPI). All the properly stained sections on coverslips were examined using a laser-scanning confocal microscope (Zeiss LSM780, Carl Zeiss, Jena, Germany); imaging software (Zen 2011, black edition, Carl Zeiss MicroImaging GmbH, 1997-2011) and AlphaEase FC (Alpha Innotech, San Leandro, CA, USA) across the entire image field of regions of interest sampled from each group under appropriate magnification (30×~100×) in 3 to 5 independent experiments. For tissue fibrosis detection, a Masson's trichrome staining protocol was followed. The above experiments were conducted to confirm whether administration of NRICM102 can reduce the effect of spike protein subunit 1 (S1) in lung tissue, thereby inhibiting neutrophil infiltration and inflammatory response; and to confirm whether administration of NRICM102 can reduce the expression of prothrombotic factors (vWF and PAI-1) and the formation of NET (CitH3) in lung tissue, thereby inhibiting pulmonary embolism.

Results

Figure 6A:
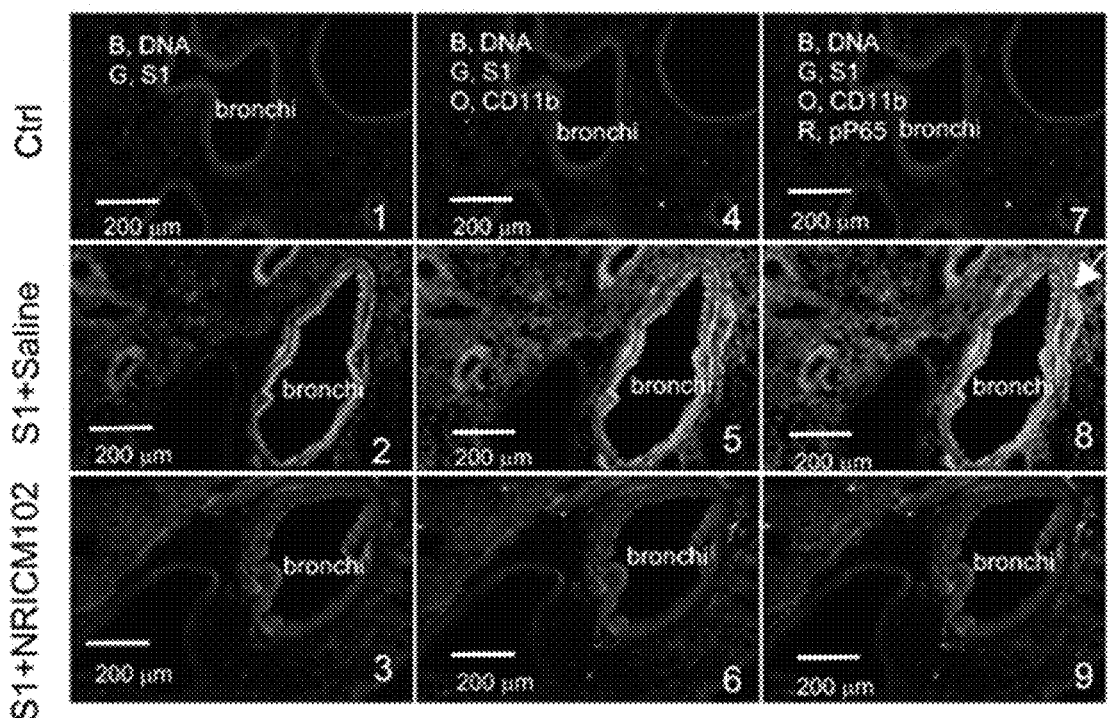
FIGS. 6A-6D are schematic diagrams of the effect of NRICM102 on the changes of spike protein and lung disease (72 hours) in K18-hACE2 mice induced by SARS-COV-2 spike protein.
Figure 6B:
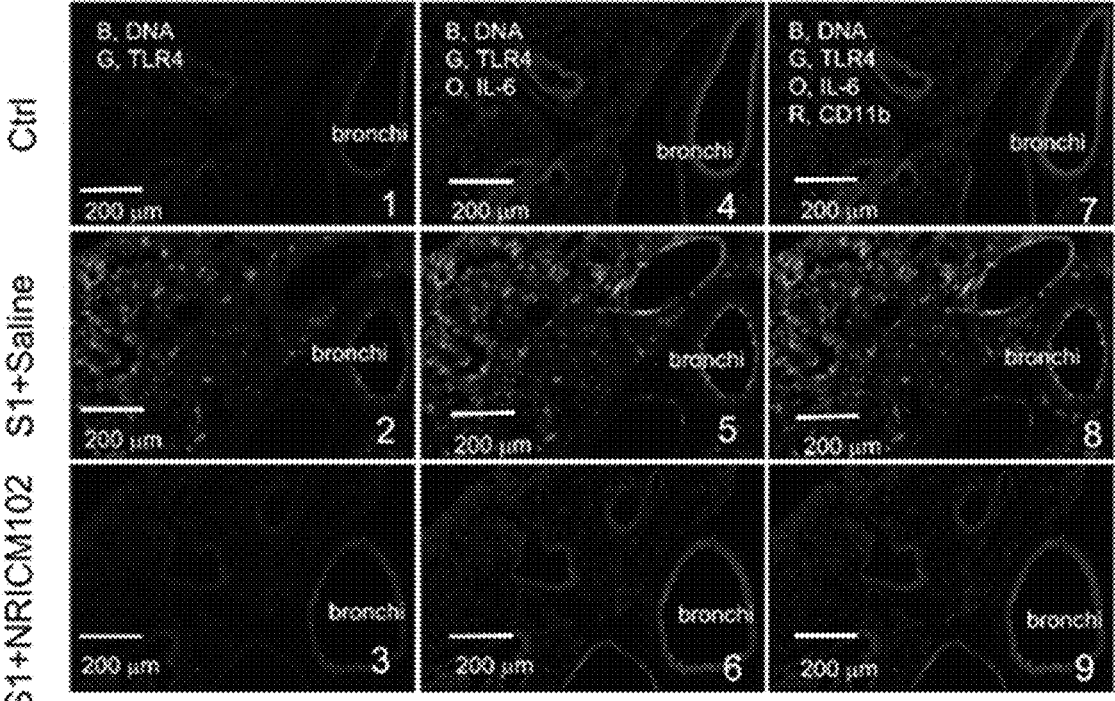
Figure 6C:
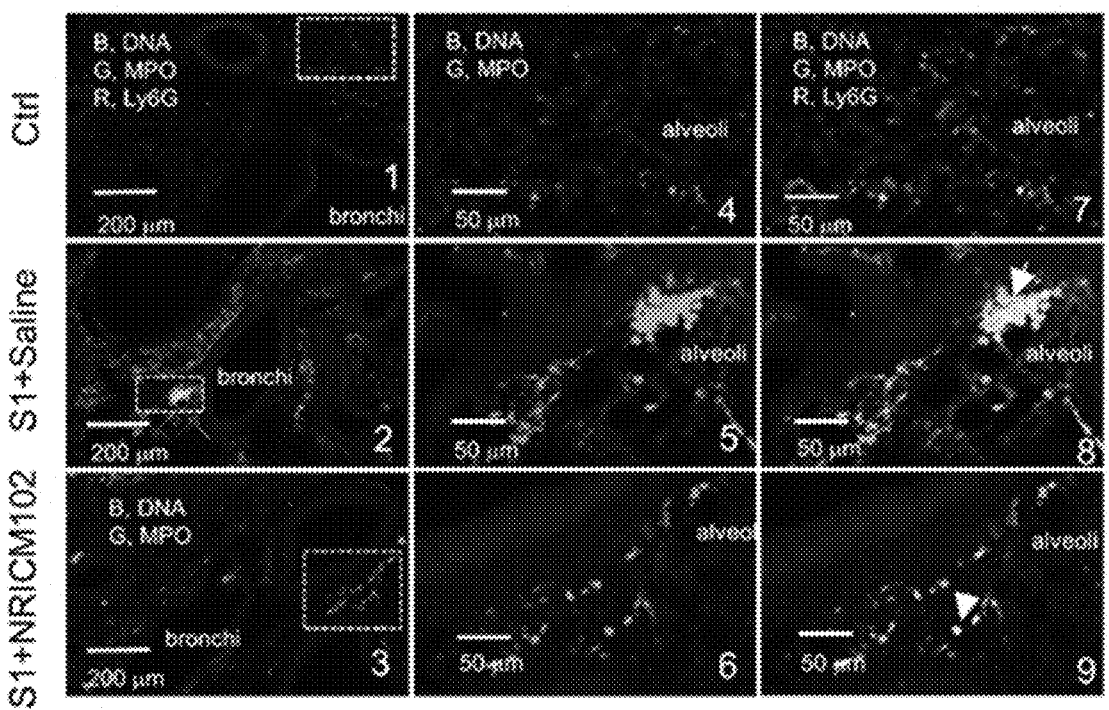
Figure 6D:
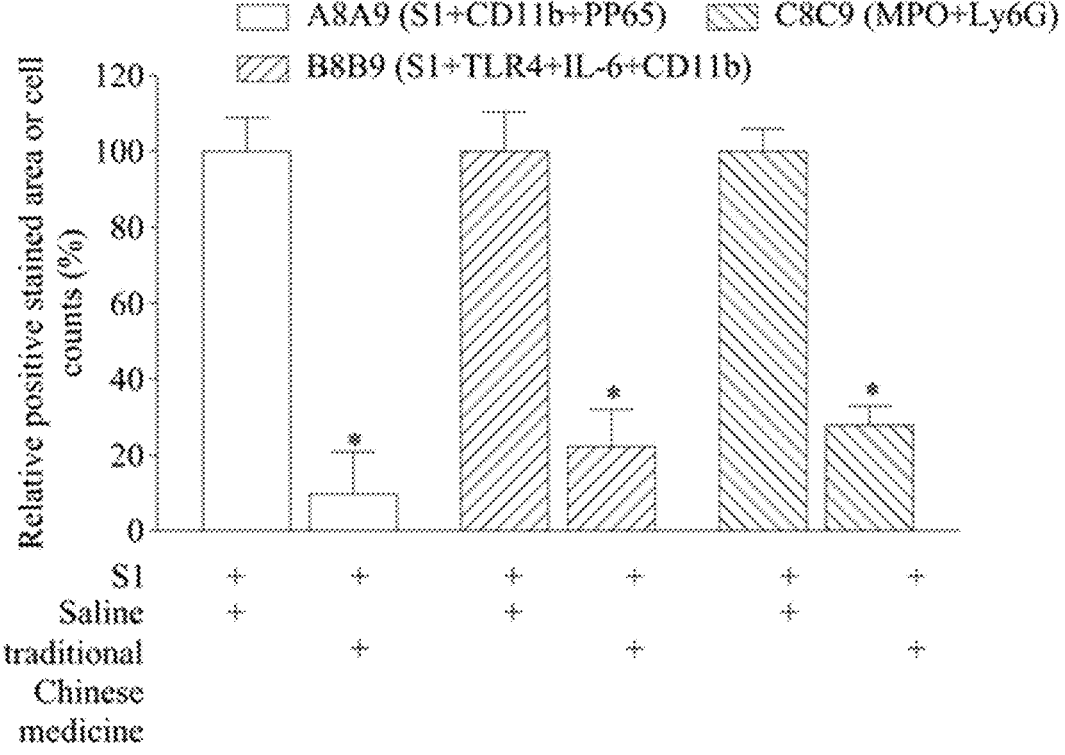

Please refer to FIGS. 6A-6D, FIGS. 6A-6D are schematic diagrams showing the effect of NRICM102 on the changes of spike protein and lung disease (72 hours) in K18-hACE2 mice with lung injury induced by SARS-COV-2 spike protein. As shown in FIGS. 6A-6C, S1 accumulated to high levels in the bronchi and bronchioles, and the accumulation was accompanied by strong neutrophil and monocyte infiltration (CD11b and Ly6G) and strong inflammatory responses, including the expression of p-NFκB P65, MPO, TLR4 and IL-6; while in the NRICM102-administered group, the accumulation of S1 and the aforementioned inflammatory markers (S1, CD11b, Ly6G p-NFκB P65, MPO, TLR4 and IL-6) level was significantly reduced; in addition, the statistical summary of the selected labeled fluorescent staining (relative staining area or cell count (%)) was shown in FIG. 6D. Therefore, the above experimental results prove that NRICM102 can indeed inhibit neutrophil infiltration and inflammatory response.

Furthermore, please refer to FIGS. 7A-7H, FIGS. 7A-7H are schematic diagrams showing the effect of NRICM102 on pulmonary thrombosis, fibrotic factor expression and apoptosis induced by SARS-COV-2 spike protein in K18-hACE2 mice. It shown in FIG. 7A that after S1 induction, vWF and PAI-1 proteins are highly expressed in lung tissue, and from FIG. 7B and FIG. 7C, it can be seen that strong NET (CitH3) formation and neutrophil infiltration occurred in lung tissue; however, the expression levels of the aforementioned prothrombotic factors (vWF, PAI-1, and NET) were significantly reduced by administration of NRICM102

Figure 7A:
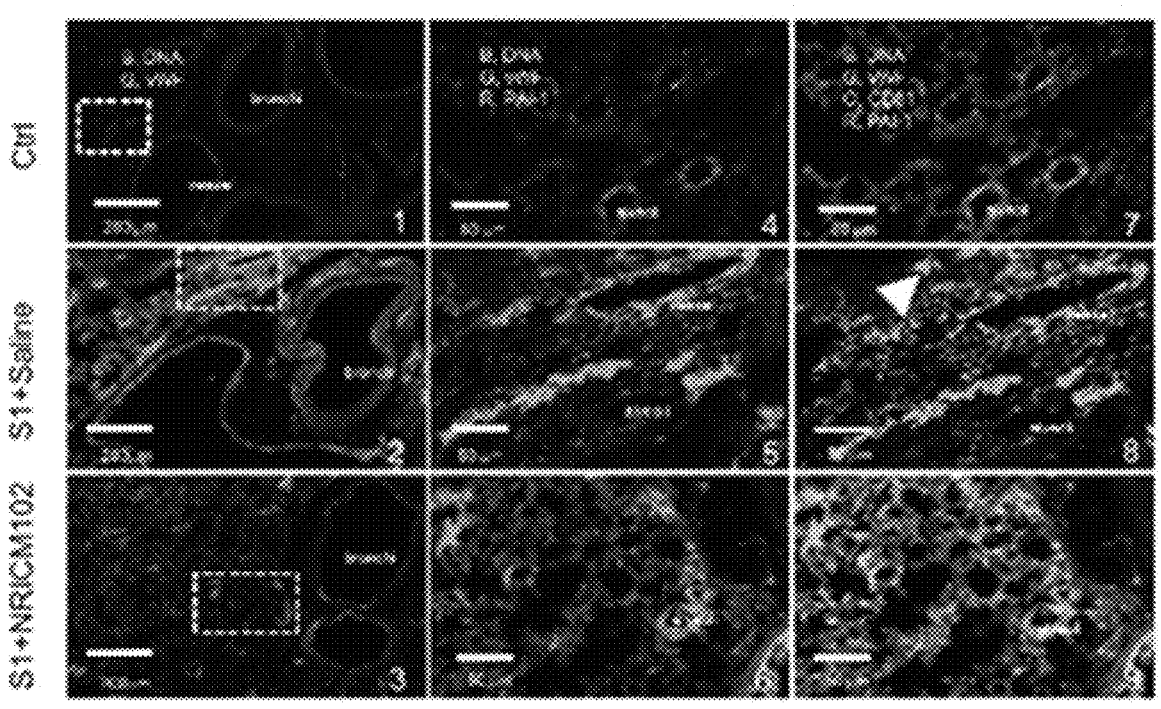
FIGS. 7A-7H are schematic diagrams of the effect of NRICM102 on pulmonary thrombosis, fibrotic factor expression and apoptosis induced by SARS-COV-2 spike protein in K18-hACE2 mice.
Figure 7B:
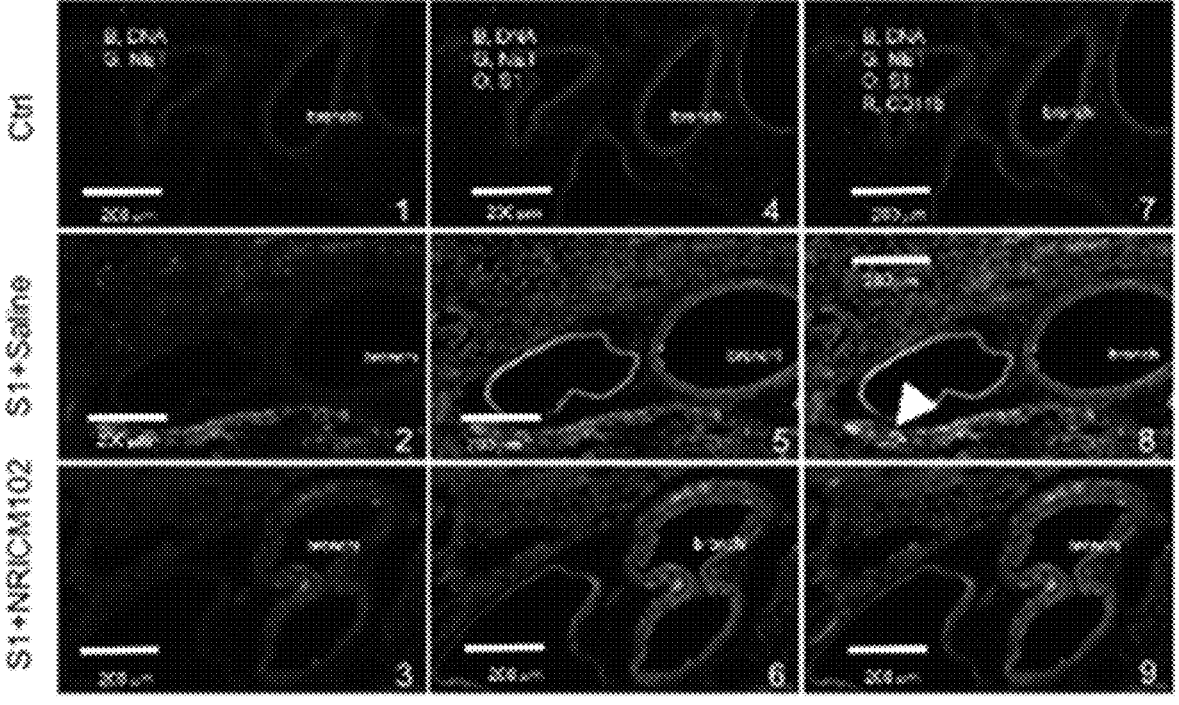
Figure 7C:
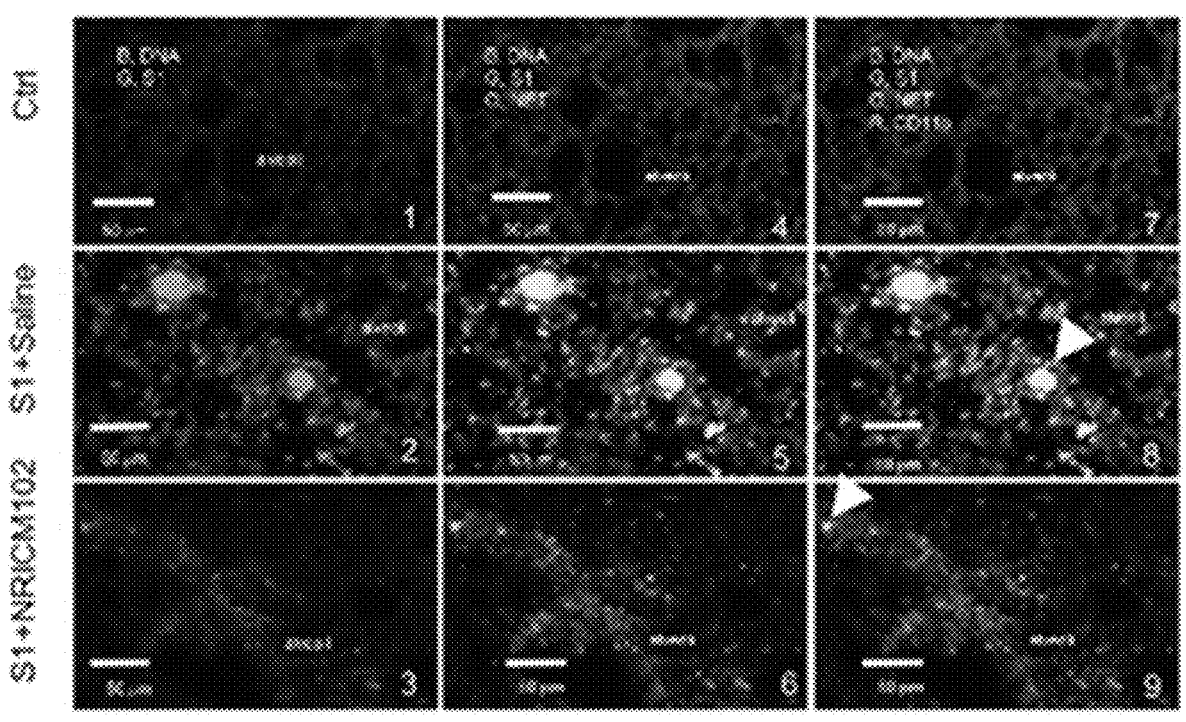
Figure 7D:
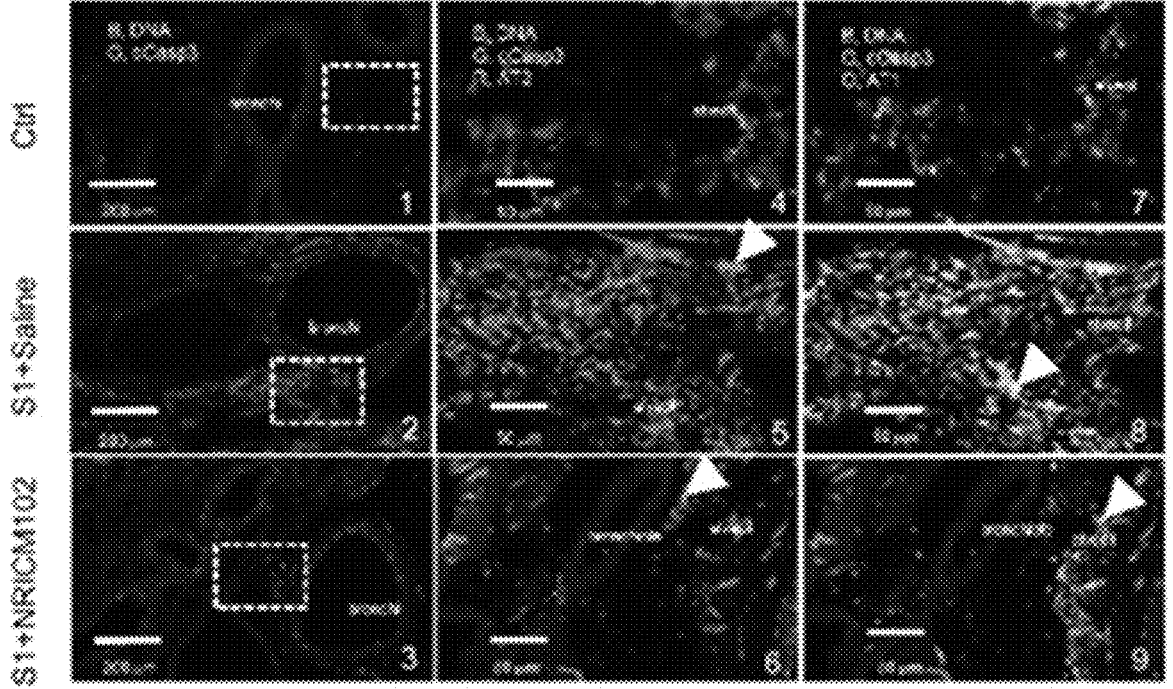

Next, the loss of AT1 and AT2 alveolar cells in S1-induced mice was examined by inducing apoptosis; as shown in FIG. 7D, significant expression of cleaved caspase 3 and cCasp3 indicates that S1 induces strong apoptosis around lung tissue, while administration of NRICM102 significantly reduces apoptosis (cCasp3) and loss of AT1, AT2 alveolar cells.

Figure 7E:
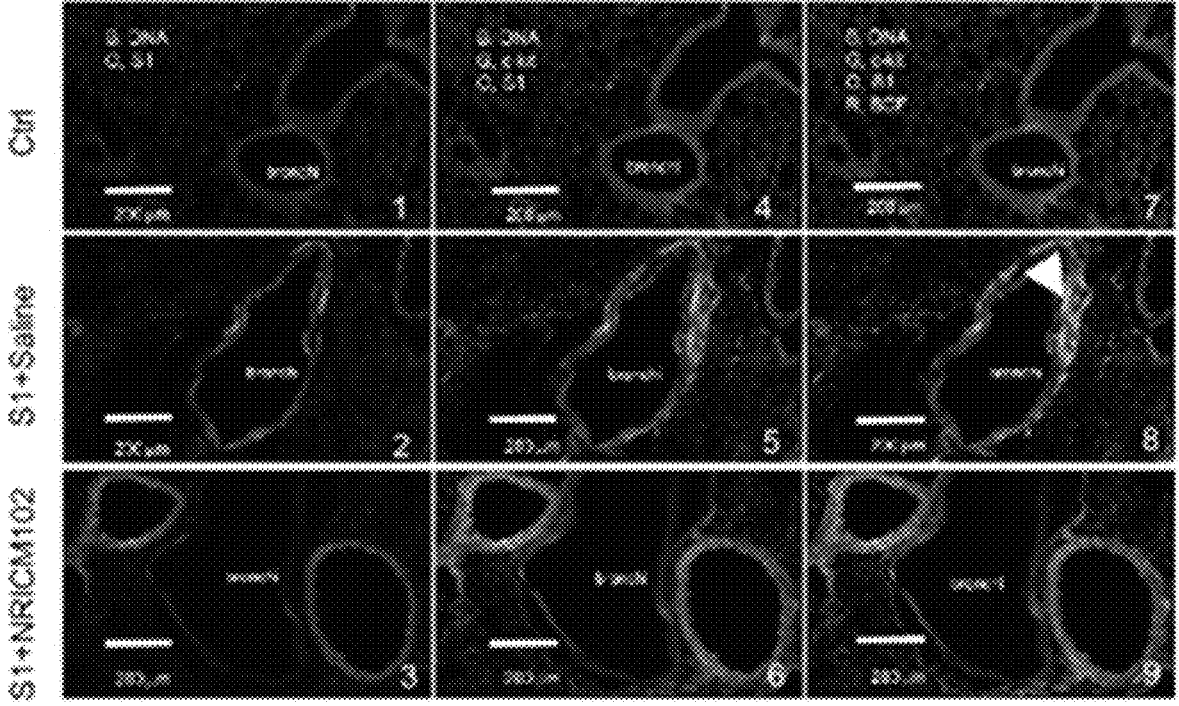
Figure 7F:
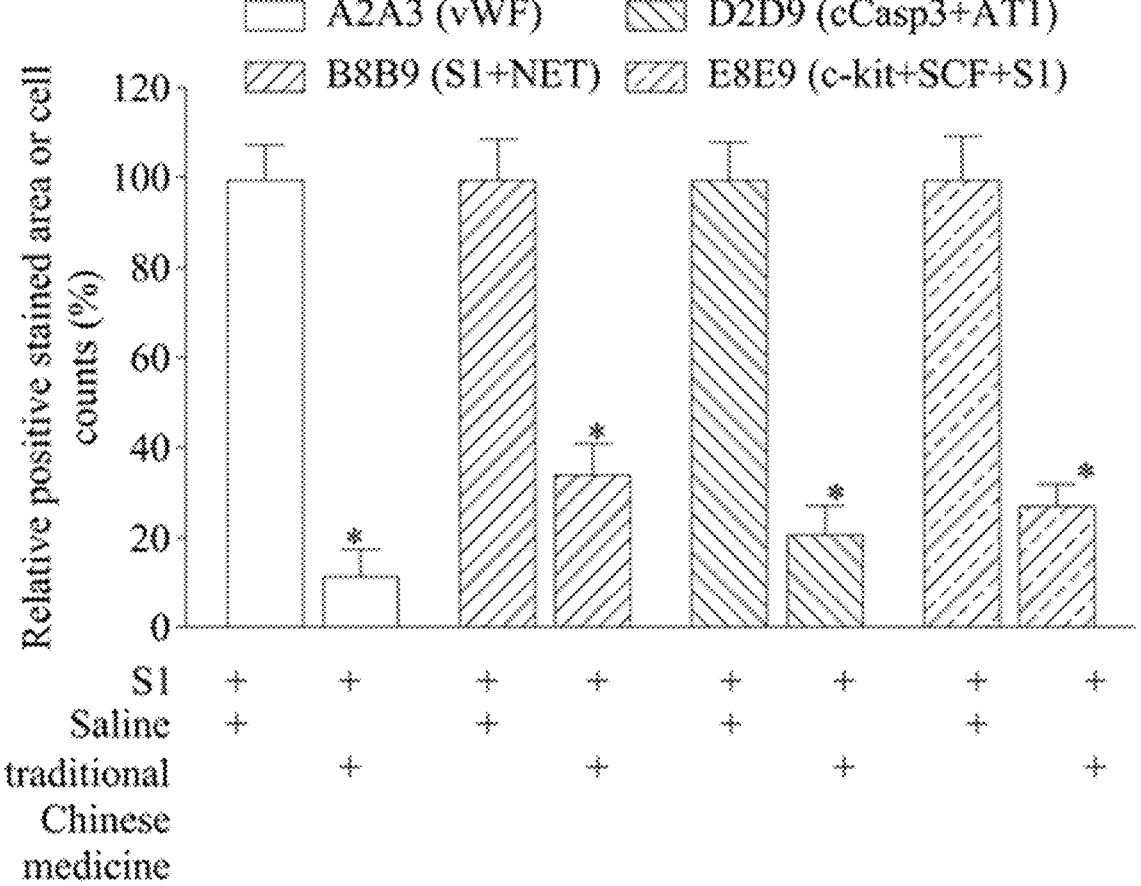
Figure 7G:
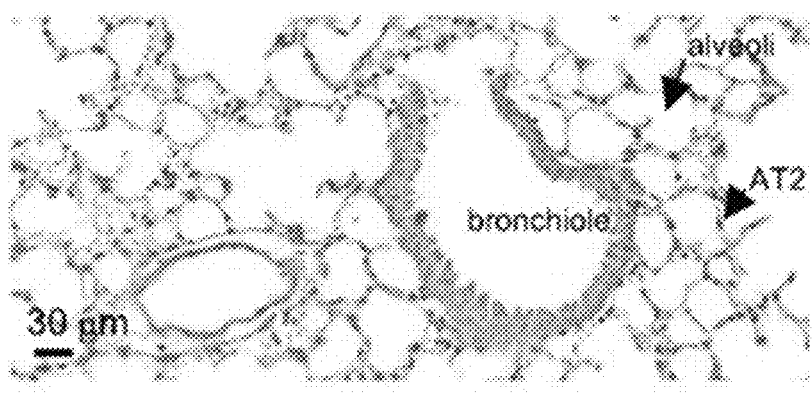
Figure 7G:
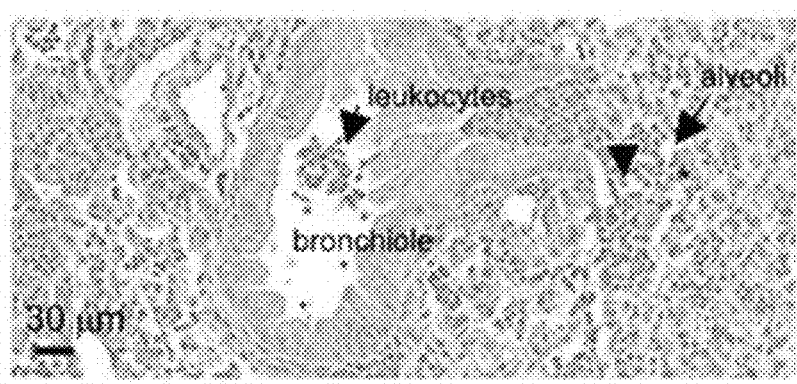
Figure 7G:
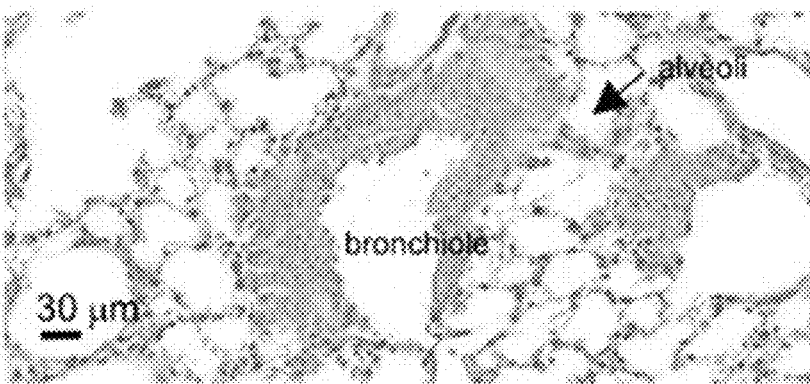
Figure 7H:
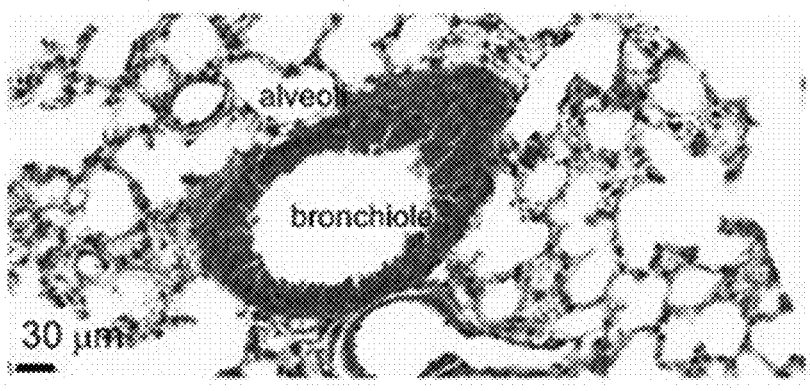
Figure 7H:
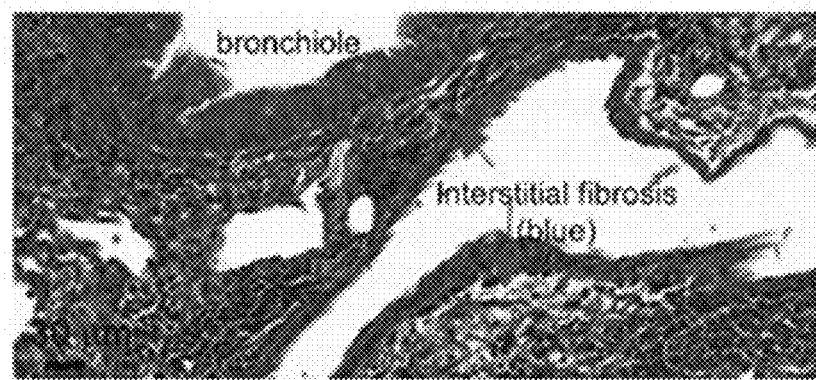
Figure 7H:
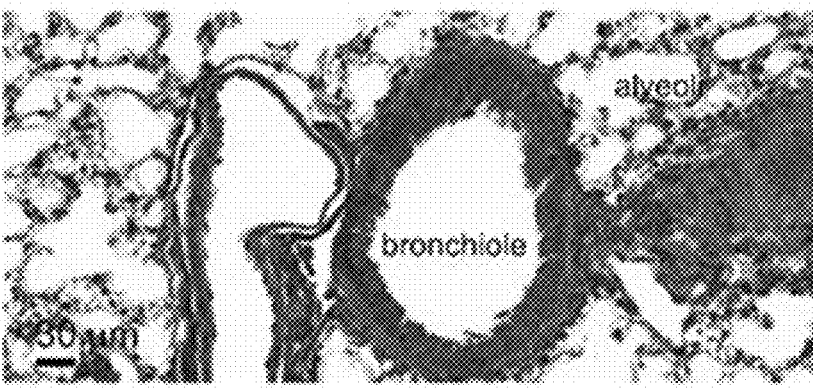

Finally, examine whether the expression levels of fibrosis factors (c-Kit and stem cell factor (SCF)) in the lung tissue induced by S1 are increased; FIG. 7E shows that in the lung tissue induced by S1, fibrosis Factors (c-Kit and SCF) were strongly expressed in the peribronchioles, while administration of NRICM102 significantly reduced the expression levels of fibrotic factors. As shown in FIG. 7F and FIG. 7G, the statistical summary of the positive fluorescent staining (relative staining area or cell count (%) of the selected markers was clearly observed in the S1+saline group. However, it was not observed in the control group (Ctrl) and S1+NRICM102 group. The results of Masson's trichrome staining for tissue fibrosis detection in FIG. 7H showed that typical tissue fibrosis (blue part) was clearly observed in the S1+saline group, but not in the Ctrl group, while the tissue fibrosis effect was significantly reduced in the S1+NRICM102 group. Therefore, the above results prove that NRICM102 can indeed treat pulmonary embolism and pulmonary fibrosis.

Embodiment 7

Monocyte Isolation and Cytokine Array Assay:

Peripheral blood mononuclear cells (PBMCs) are isolated from blood samples of healthy donors; that is, PBMCs are isolated from whole blood using Ficoll-Paque™ density gradient centrifugation, and monocytes (98% pure CD14$^+$) were isolated from PBMCs by using a classical monocyte isolation kit (Miltenyi Biotec). The isolated monocytes were treated with S1 (100 g/mL) and NRICM102 for 24 hours. The supernatant (ie, isolated monocytes) was then subjected to cytokine assays using the Human XL Cytokine Array Kit (Cytokine Array, R&D).

Results

Figure 8:
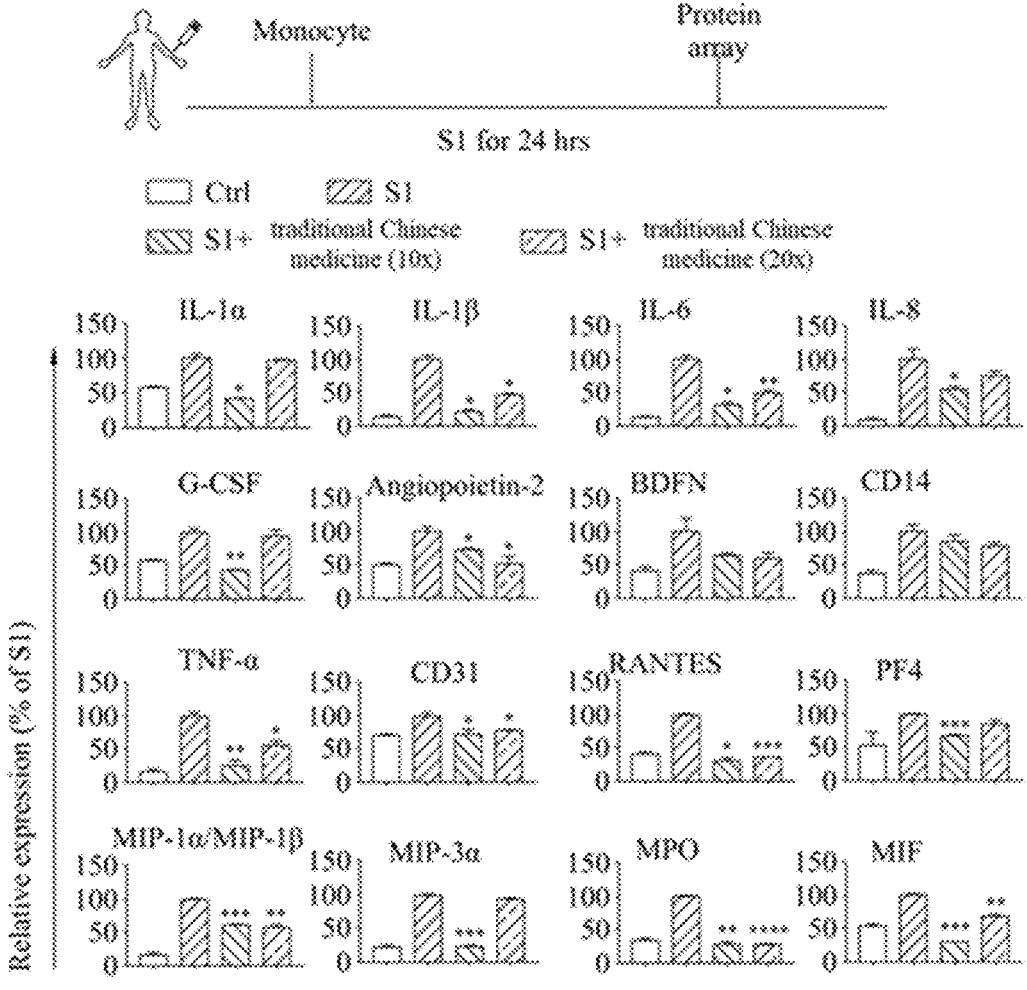
FIG. 8 is a schematic diagram of the effect of NRICM102 on the expression of cytokines and chemokines induced by SARS-COV-2 spike protein in human monocytes

Please refer to FIG. 8, FIG. 8 is a schematic diagram showing the effect of NRICM102 on the expression of cytokines and chemokines induced by SARS-COV-2 spike protein in human monocytes. As shown in FIG. 8, NRICM102 significantly inhibited the induced expression of various chemokines and cytokines which are factors related to cytokine storm, including TNF-α, CD31, RANTES, platelet factor 4 (PF4), IL-1α, IL-1β, IL-6, IL-8, macrophage inflammatory proteins-1α and 1β (MIP-1α, MIP-1β), MIP-3α, myeloperoxidase (MPO), macrophage migration inhibitory factor (MIF), Granular Leukocyte Colony Stimulating Factor (G-CSF) and Angiopoietin-2.

Embodiment 8

Epithelial Mesenchymal Transition (EMT) and Fibroblast to Myofibroblast Transformation (FMT) Assay:

EMT of bronchial epithelial cells and fibroblast to myofibroblast transformation (FMT) are the key process in the development of pulmonary fibrosis. Epithelial cells which have undergone EMT which subsequently promotes the generation of FMT and fibrogenesis. TGF-B has been reported to induce EMT and FMT which are characterized by the expression of fibronectin (FN1) and alpha smooth muscle actin (α-SMA), respectively. Thus, when EMT occurs in bronchial epithelial cells exposed to TGF-β, fibronectin (FN1) and alpha smooth muscle actin (α-SMA) expression are considered the markers of TGF-β-induced EMT and FMT. In order to evaluate the effect of NRICM102 on EMT of human bronchial epithelial cells (BEAS-2B), the cells were treated with TGF-β or co-treated with TGF-β and NRICM102. And in order to evaluate the effect of NRICM102 on FMT of human fibroblast cells (HFL-1 cells), the cells were treated with TGF-β or co-treated with TGF-β and NRICM102, the processes are as follows:

For EMT assay, BEAS-2B cells were cultured in dishes coated with bovine serum albumin (BSA, purchased from Bionovas), native fibronectin human protein (purchased from Gibco) and bovine collagen I (purchased from Gibco). The cells were grown at 37° C. under 5% $CO_2$ in bronchial epithelial cell growth basal medium (BEGM, purchased from Lonza). BEAS-2B cells ($6\times10^3$) were seeded in a 96-well black plate (purchased from Thermo Fisher Scientific) and incubated in BEGM for 24 hrs. Then, the cells were stimulated with 10 ng/ml TGF-β (purchased from PeproTech) and incubated for 3 days.

For FMT assay, HFL-1 cells ($6\times10^3$) were seeded in a 96-well black plate (purchased from Thermo Fisher Scientific) and incubated in F-12K medium with 10% FBS for 24 hrs. The cells were washed 3 times with PBS buffer and starved in F-12K medium with 0.1% FBS for 24 h. Then, the cells were replaced with F-12K medium with 0.5% FBS containing 10 ng/mL TGF-β (purchased from PeproTech) and incubated for 3 days.

The BEAS-2B and HFL-1 cells were fixed with cold methanol (−20° C.) for 30 min at room temperature Following fixation, permeabilization, and blocking, the BEAS-2B and HFL-1 cells were incubated with a fibronectin antibody (FN1, 1:800 dilution, Cell Signaling) or with alpha smooth muscle actin antibody (α-SMA, 1:800 dilution, Cell Signaling) overnight at 4° C., respectively. After washing, the cells were incubated with Alexa Fluor 488 anti-rabbit IgG (1:1000 dilution, Cell Signaling). The cells were incubated with DAPI (5 μg/mL, purchased from Thermo Fisher Scientific) for nuclear staining. Images were captured with a Cytation 5 Cell Imaging Multi-Optical Detector.

Data analysis was performed using GraphPad Prism software (version 9.0, GraphPad Software, San Diego, CA), and the results of the analysis are presented as mean±SEM (standard deviation). Statistical analysis involved one-way ANOVA, followed by S-N-K t-test analysis. Differences were considered statistically significant at p<0.05. In each figure, ** represents p<0.01.

Results

Figure 9A:
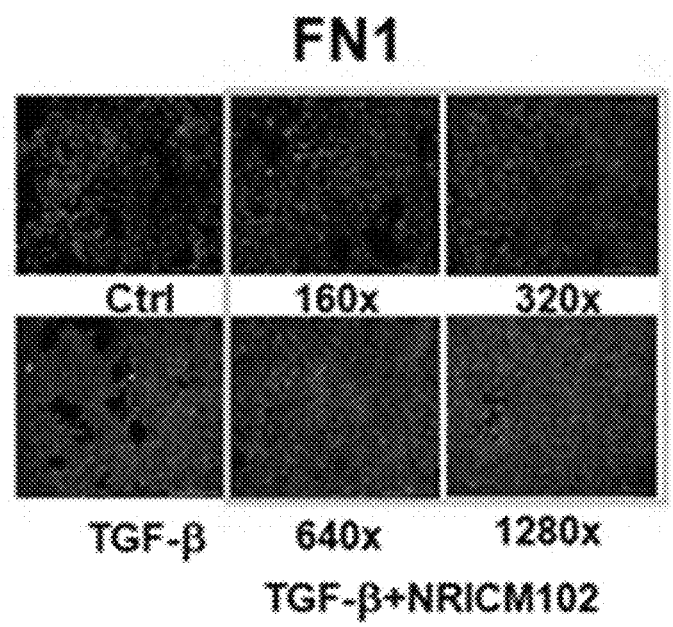
FIGS. 9A and 9B are schematic diagrams of the effect of NRICM102 on TGF-β-induced epithelial-mesenchymal transition (EMT) and fibroblast to myofibroblast transformation (FMT)
Figure 9A:
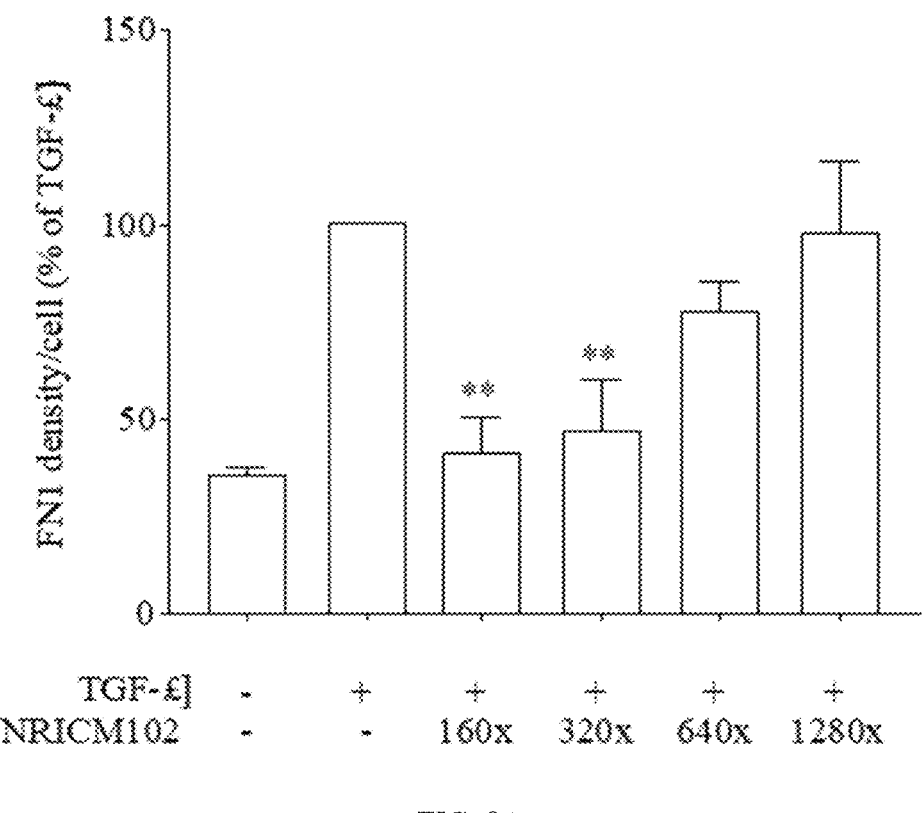
Figure 9B:
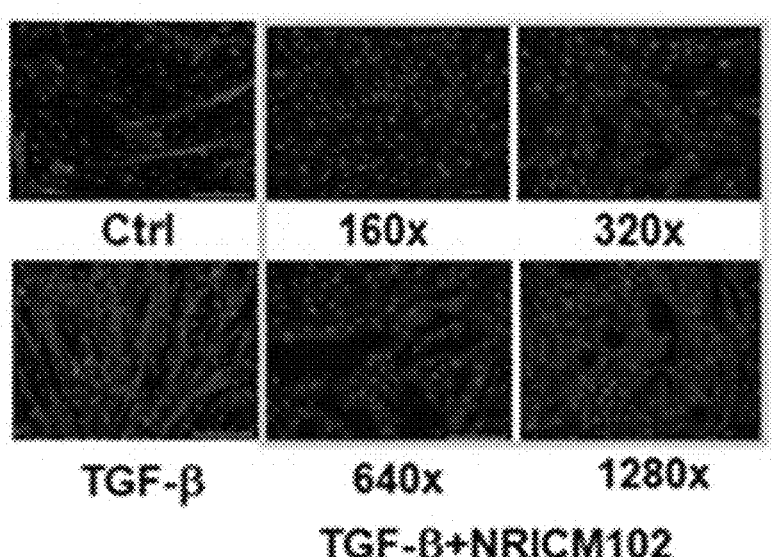
Figure 9B:
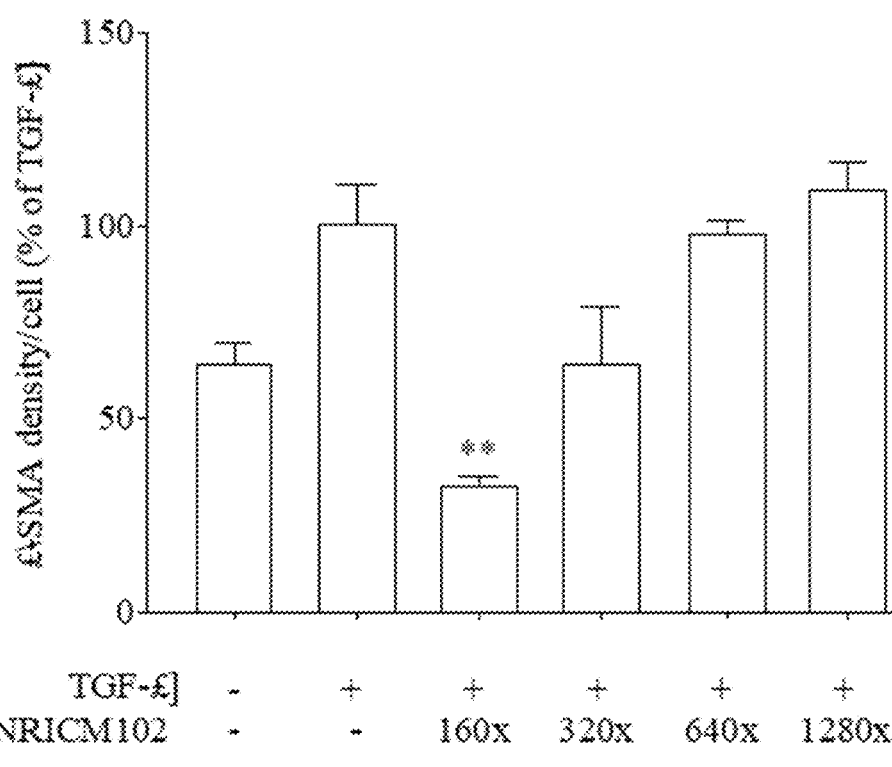

Please refer to FIGS. 9A and 9B, FIGS. 9A and 9B are schematic diagrams showing the effect of NRICM102 on TGF-B-induced epithelial-mesenchymal transition (EMT) and fibroblast to myofibroblast transformation (FMT). The results showed that TGF-treatment significantly increased the expression of FN1 and α-SMA compared with that in the untreated cells. NRICM102 treatment significantly decreased the expression of FN1 and α-SMA in a dose-dependent manner compared with the expression in the TGF-β treated cells (FIGS. 9A and 9B). These results suggest that NRICM102 exhibited the capability to inhibit the TGF-β induced transition of BEAS-2B cells from bronchial epithelial cells to a mesenchymal-like phenotype and formation of HFL-1 cells from fibroblast to myofibroblast.

Experimental Example 1

In order to determine the efficacy of NRICM102 (i.e. Taiwan Chingguan Erhau) on patients actually infected with COVID-19, experimental cooperation was carried out with several hospitals. According to the hypoxia symptoms of individual COVID-19 patients, the doctors used whether additional oxygen from an oxygen machine is required as the criteria for judging mild symptoms or moderate to severe symptoms. Patients who do not need additional oxygen supply (i.e., patients with mild symptoms) are prescribed NRICM101 (i.e., Taiwan Chingguan Yihau) for treatment, results. Also, refer to Table 2 below, which present associations between the traditional Chinese medicine composition use and the endpoint.

TABLE 2

| Analysis | NRICM101 Intubation or ICU Admission | NRICM102 Death |
|---|---|---|
| | No. of events/no. of patients at risk (%) | |
| TCM + Usual Care | 0/164 (0.00) | 7/126 (5.56) |
| Usual Care | 14/181 (7.73) | 42/240 (17.50) |
| Relative Risk (95% CI) | —&^ | 40.80% (20.54%-81.12%)^ |
| | Propensity score analyses - with matching | |
| TCM + Usual Care (%) | 0/151 (0.00) | 7/123 (5.69) |
| Usual Care (%) | 14/151 (9.27) | 27/123 (21.95) |
| Relative Risk (95% CI) | —&* | 25.93% (11.73%-57.29%)* |
| Hazard Ratio (95% CI) | —$# | 23.17% (10.36-51.82%)# |

&is represented as Seriously underestimated relative risk (95% CI) = 15.8% (3.6%-68.3%) for unmatched data and 14.3% (3.3%-71.8%) for matched data when we included 2 censored cases as the endpoint.
^is represented as The chi-square test was used for unmatched data (p = 0.002 for death and p = 0.006 when we set 2 censored cases as intubation or ICU admission).
*is represented as McNemar's test compared the proportion of intubation or ICU admission (p = 0.003) and death (p < 0.001) for matched data. The power of McNemar's test being larger than 0.852 for NRICM101 and 0.929 for NRICM102 indicates that the significance of both is not due to chance.
$is represented as Seriously underestimated hazard ratio = 13.58% (3.40-54.21%) when we set 2 censored cases as the endpoint by the marginal Cox model.
is represented as Hazard ratio by marginal Cox regression and p < 0.001 by stratified log-rank test for both NRICM101 and NRICM102.

and patients who need oxygen supply (i.e., patients with moderate to severe symptoms) were prescribed NRICM102 for treatment, both traditional Chinese medicine composition were taken orally three times a day.

Figure 10:
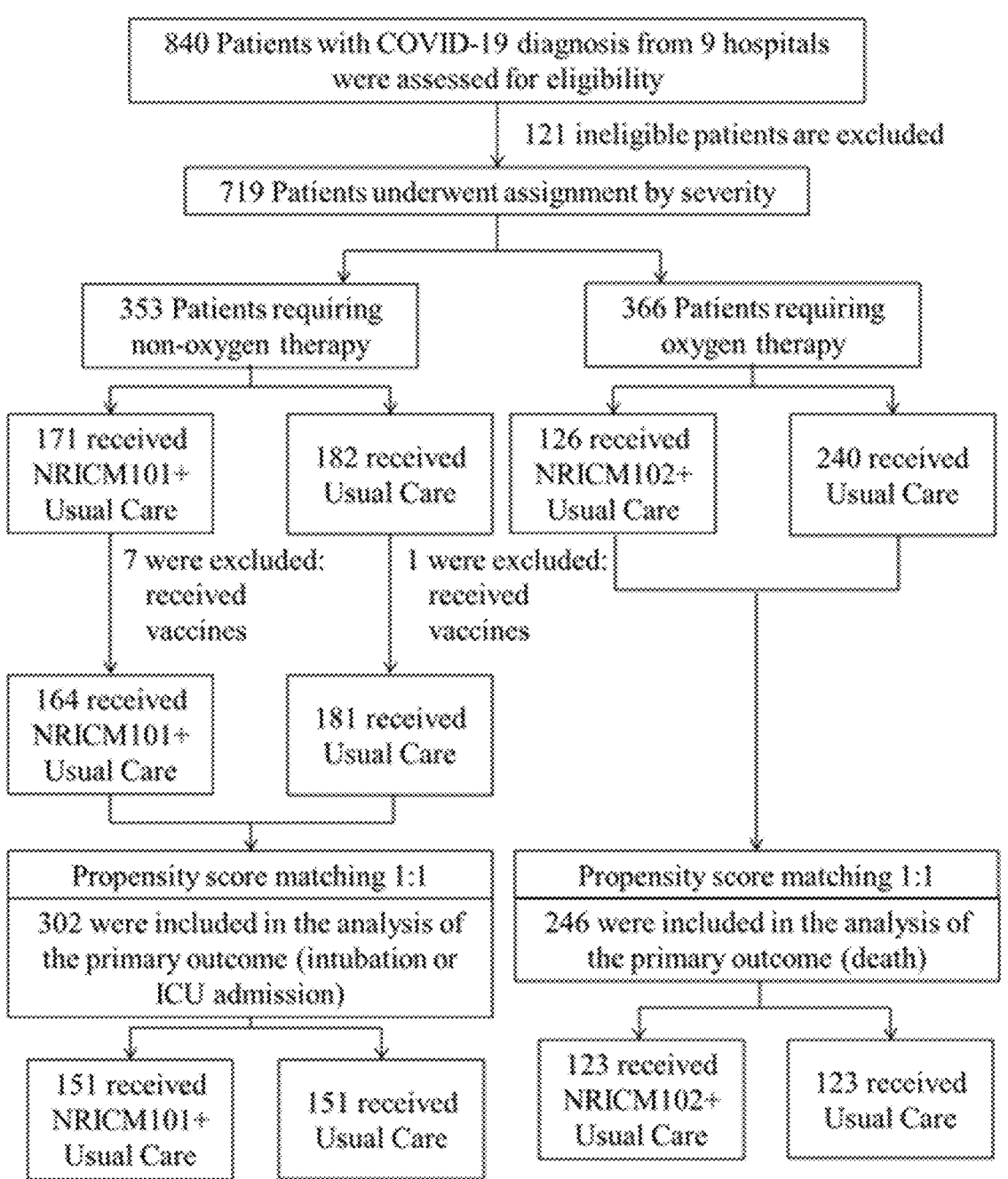
FIG. 10 is a schematic flow chart of the clinical study.

Please refer to FIG. 10, FIG. 10 is a schematic flow chart of the clinical study screening process. 840 patients with Covid-19 were admitted to the partnered hospitals between May 1 and Jul. 26, 2021. Among them, 121 patients were excluded from the base cohort for being under 20 years of age, previously treated elsewhere, admitted for other diseases, critically ill, or hospitalized for less than 2 days. The base cohort of 719 patients was initially divided into the mild-to-moderate group of 353 cases who required no oxygen therapy (non-oxygen group) and the severe-to-critical group of 366 cases who required oxygen therapy (oxygen group), with the former receiving NRICM101 or not and the latter receiving NRICM102 or not. After further excluding those who were vaccinated from the non-oxygen therapy group (not for the oxygen therapy group because vaccination was no longer a factor at this stage). Finally, 302 patients who did (151) and did not (151) receive NRICM101 as well as 246 patients who did (123) and did not (123) receive NRICM102 were included in the analysis. Among them, patients who did not receive NRICM101 and NRICM102 treatment only received usual care.

The patients who received treatment were those diagnosed as positive by PCR between May 1, 2021 and Jul. 26, 2021, and were continuously observed for 30 days. For the group without oxygen therapy, the primary endpoint was the subsequent need for intubation or ICU admission to the group with oxygen therapy, the primary endpoint was death. Patients were followed up from the time of hospital admission until one of the following events occurred: death, intubation, or 30 days of follow-up; those patients without a primary endpoint event had their data censored as of day 30 following hospital admission.

Results

Figure 11A:
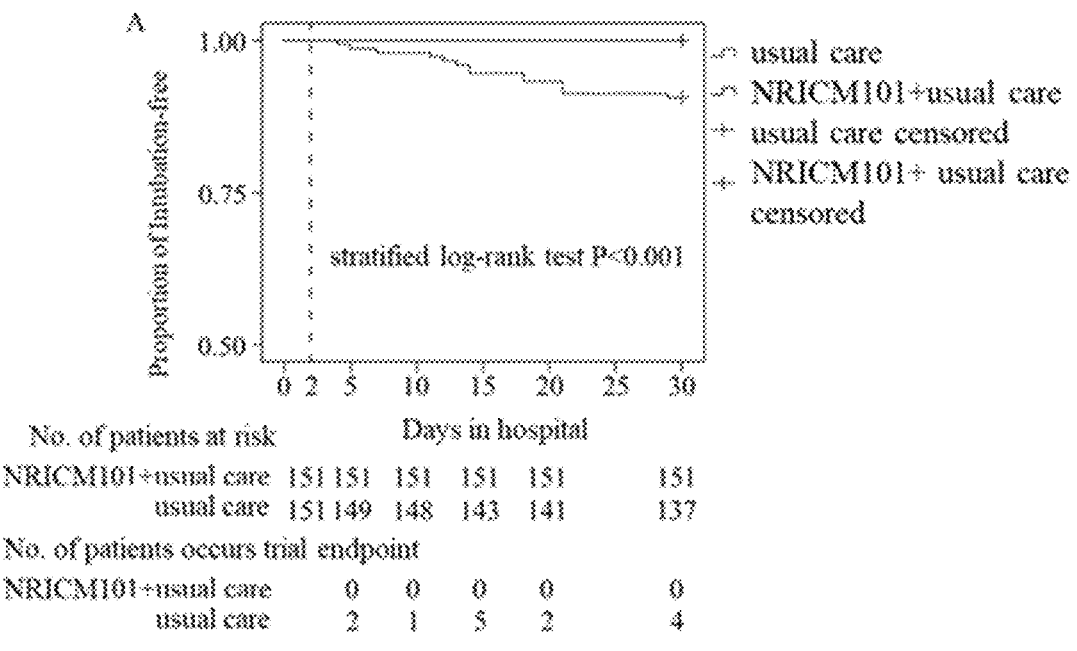
FIGS. 11A and 11B are schematic diagrams of the results analysis of the clinical study.
Figure 11B:
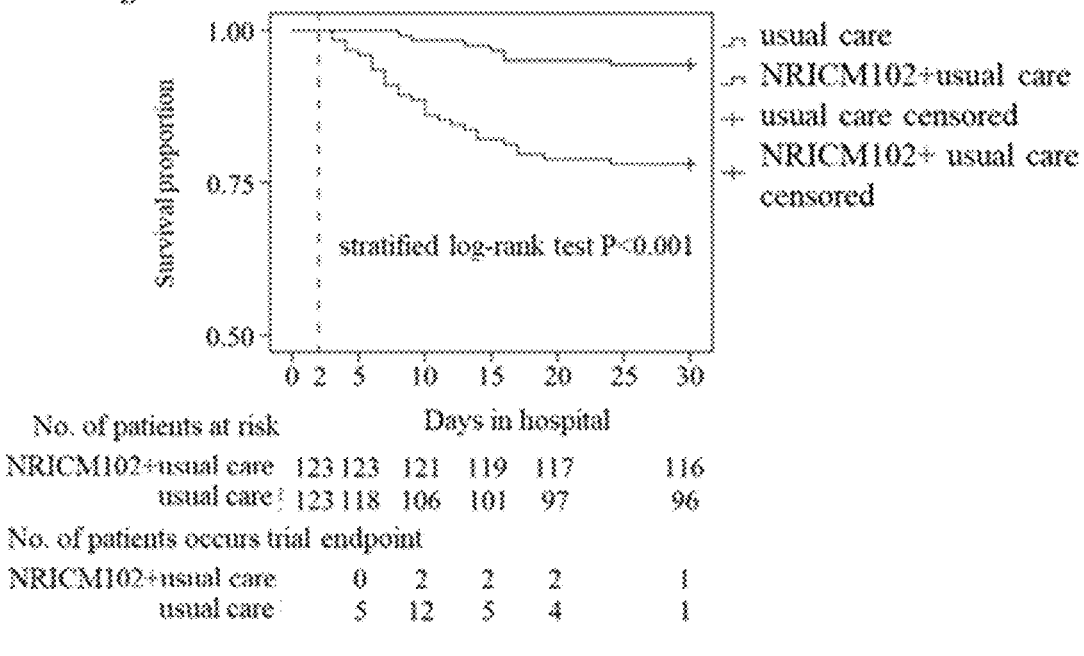

Please refer to FIGS. 11A and 11B, FIGS. 11A and 11B are schematic diagrams of the analysis of clinical study & is represented as Seriously underestimated relative risk (95% CI)=15.8% (3.6%-68.3%) for unmatched data and 14.3% (3.3%-71.8%) for matched data when we included 2 censored cases as the endpoint.

^ is represented as The chi-square test was used for unmatched data (p=0.002 for death and p=0.006 when we set 2 censored cases as intubation or ICU admission).

* is represented as McNemar's test compared the proportion of intubation or ICU admission (p=0.003) and death (p<0.001) for matched data. The power of McNemar's test being larger than 0.852 for NRICM101 and 0.929 for NRICM102 indicates that the significance of both is not due to chance.

$ is represented as Seriously underestimated hazard ratio=13.58% (3.40-54.21%) when we set 2 censored cases as the endpoint by the marginal Cox model.

is represented as Hazard ratio by marginal Cox regression and p<0.001 by stratified log-rank test for both NRICM101 and NRICM102.

During the 30-day observation period, 14 patients (4.06%) in the non-oxygen group had a primary endpoint event (intubation or ICU admission), and 49 patients (13.39%) in the oxygen group died. No patient receiving NRICM101 plus usual care experienced the endpoint, while 14 (9.27%) in the group receiving only usual care were intubated or admitted to ICU. The numbers of deceased patients were 7 (5.69%) in the group receiving NRICM102 plus usual care and 27 (21.95%) in the group receiving usual care.

We present a seriously underestimated relative risk 15.8% (95% confidence interval [CI], 3.6%-68.3%) for unmatched data and 14.3% (95% CI, 3.3%-71.8%) for matched data when we set 2 censored cases as intubation or ICU admission. Additionally, the results of marginal Cox regression and log-rank tests for days of without intubation or transfer to ICU after matching indicated a significant association between NRICM101 use and usual care (hazard ratio, 13.58%; 95% CI, 3.40%-54.21%). Patients who did not receive NRICM102 were more likely to have experienced a primary endpoint event than were patients who did (relative risk, 40.80%; 95% CI, 20.54%-81.12%) in the unmatched data analysis.

The results of marginal Cox regression, MeNemar's test and log-rank tests after propensity score matching indicated a significant association between NRICM102 use and death (relative risk, 25.93%; 95% CI, 11.73%-57.29%; hazard ratio, 23.17%; 95% CI, 10.36%-51.82%). Regarding the impact of potential confounders, the e-value was 7.1756 which is bigger than the RR of corticosteroids. Hence, the treatment effect of TCM was robust.

In conclusion, the traditional Chinese medicine composition NRICM102 (namely Taiwan Chingguan Erhau) according to the present invention can indeed treat patients with moderate or severe symptoms of COVID-19.

The present disclosure disclosed herein has been described by means of specific embodiments. However, numerous modifications, variations and enhancements can be made thereto without departing from the spirit and scope of the disclosure set forth in the claims.

The invention claimed is:

1. A method of treating moderate or severe symptoms of COVID-19 using a plant composition, wherein the plant composition comprises: Prepared Monkshood Daughter Root, Fragrant Solomonseal Rhizome, Indian Bread, *Pinellia* tuber, Oriental Wormwood Herb, *Scutellaria* Root, Mongolian Snakegourd Fruit, *Magnolia* Bark, Heartleaf *Houttuynia* Herb, and Baked Licorice Root and Rhizome.

2. The method according to claim 1, wherein contents of each component of the plant composition is as follows: 1 part by weight of an aqueous extract of Prepared Monkshood Daughter Root, 1.5 parts by weight of an aqueous extract of Fragrant Solomonseal Rhizome, 2.5 parts by weight of an aqueous extract of Indian Bread, 1.5 part by weight of an aqueous extract of *Pinellia* tuber, 2.5 parts by weight of an aqueous extract of Oriental Wormwood Herb, 1.5 parts by weight of an aqueous extract of *Scutellaria* Root, 2.5 parts by weight of an aqueous extract of Mongolian Snakegourd Fruit, 1.5 parts by weight of an aqueous extract of *Magnolia* Bark, 5 parts by weight of an aqueous extract of Heartleaf *Houttuynia* Herb, and 1 part by weight of an aqueous extract of Baked Licorice Root and Rhizome.

3. The method according to claim 1, wherein the plant composition inhibits binding of spike protein of coronavirus to type II angiotensin-converting enzyme (ACE2).

4. The method according to claim 1, wherein the plant composition inhibits an activity of viral 3CL protease.

5. A method of treating moderate or severe symptoms of COVID-19 using a traditional Chinese medicine composition, wherein the traditional Chinese medicine composition comprises: Prepared Monkshood Daughter Root, Fragrant Solomonseal Rhizome, Indian Bread, *Pinellia* tuber, Oriental Wormwood Herb, *Scutellaria* Root, Mongolian Snakegourd Fruit, *Magnolia* Bark, Heartleaf *Houttuynia* Herb, and Baked Licorice Root and Rhizome.

6. The method according to claim 5, wherein contents of each component of the traditional Chinese medicine composition is as follows: 1 part by weight of an aqueous extract of Prepared Monkshood Daughter Root, 1.5 parts by weight of an aqueous extract of Fragrant Solomonseal Rhizome, 2.5 parts by weight of an aqueous extract of Indian Bread, 1.5 part by weight of an aqueous extract of *Pinellia* tuber, 2.5 parts by weight of an aqueous extract of Oriental Wormwood Herb, 1.5 parts by weight of an aqueous extract of *Scutellaria* Root, 2.5 parts by weight of an aqueous extract of Mongolian Snakegourd Fruit, 1.5 parts by weight of an aqueous extract of *Magnolia* Bark, 5 parts by weight of an aqueous extract of Heartleaf *Houttuynia* Herb, and 1 part by weight of an aqueous extract of Baked Licorice Root and Rhizome.

7. The method according to claim 5, wherein the traditional Chinese medicine composotion inhibits binding of spike protein of coronavirus to type II angiotensin-converting enzyme (ACE2).

8. The method according to claim 5, wherein the traditional Chinese medicine composition inhibits an activity of viral 3CL protease.

* * * * *